(12) United States Patent
Welsh et al.

(10) Patent No.: US 7,014,654 B2
(45) Date of Patent: Mar. 21, 2006

(54) STENT DESIGNED FOR THE DELIVERY OF THERAPEUTIC SUBSTANCE OR OTHER AGENTS

(75) Inventors: Greg P. Welsh, San Jose, CA (US); Lex P. Jansen, Pleasanton, CA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 435 days.

(21) Appl. No.: 09/999,279

(22) Filed: Nov. 30, 2001

(65) Prior Publication Data

US 2003/0105511 A1 Jun. 5, 2003

(51) Int. Cl.
*A61F 2/06* (2006.01)

(52) U.S. Cl. .................................................. 623/1.15
(58) Field of Classification Search ............... 623/1.15, 623/1.16, 1.42–1.46; 606/194
See application file for complete search history.

(56) References Cited

U.S. PATENT DOCUMENTS

| | | | | |
|---|---|---|---|---|
| 5,810,767 A | 9/1998 | Klein | ............................ | 604/53 |
| 5,843,172 A | 12/1998 | Yan | ................................. | 623/1 |
| 5,876,449 A | 3/1999 | Starck et al. | ................... | 623/12 |
| 5,882,335 A | 3/1999 | Leone et al. | ................... | 604/96 |
| 5,922,020 A | 7/1999 | Klein et al. | ..................... | 623/1 |
| 5,972,027 A | 10/1999 | Johnson | ........................... | 623/1 |
| 6,042,606 A | 3/2000 | Frantzen | ......................... | 623/1 |
| 6,162,243 A | 12/2000 | Gray et al. | .................. | 623/1.11 |
| 6,190,404 B1 | 2/2001 | Palmaz et al. | ............. | 623/1.15 |
| 6,206,915 B1 | 3/2001 | Fagan et al. | ............... | 623/1.42 |
| 6,206,916 B1 | 3/2001 | Furst | .......................... | 623/1.46 |
| 6,231,598 B1 | 5/2001 | Berry et al. | ................. | 623/1.15 |
| 6,254,632 B1 * | 7/2001 | Wu et al. | .................... | 623/1.15 |
| 6,258,121 B1 | 7/2001 | Yang et al. | ................. | 623/1.46 |
| 6,273,908 B1 | 8/2001 | Ndondo-Lay | .................... | 623/1 |
| 6,273,913 B1 | 8/2001 | Wright et al. | .............. | 623/1.42 |
| 6,280,413 B1 | 8/2001 | Clark et al. | .................. | 604/104 |
| 6,379,381 B1 | 4/2002 | Hossainy et al. | ........... | 623/1.42 |
| 6,758,859 B1 * | 7/2004 | Dang et al. | ................. | 623/1.15 |
| 2001/0027340 A1 | 10/2001 | Wright et al. | | |
| 2001/0044652 A1 | 11/2001 | Moore | | |
| 2002/0007209 A1 | 1/2002 | Scheerder et al. | | |

FOREIGN PATENT DOCUMENTS

| | | |
|---|---|---|
| DE | 196 53 721 | 4/1998 |
| DE | 196 53 721 A1 | 4/1998 |
| WO | 9626689 | 9/1996 |
| WO | WO 96/26689 | 9/1996 |
| WO | WO 99/01088 | 1/1999 |
| WO | WO 99/15108 | 4/1999 |
| WO | WO 01/26584 | 4/2001 |
| WO | WO 01/26584 A1 | 4/2001 |
| WO | WO 01/66036 | 9/2001 |
| WO | WO 01/91918 | 12/2001 |

* cited by examiner

*Primary Examiner*—(Jackie) Tan-Uyen T. Ho
(74) *Attorney, Agent, or Firm*—Jones Day

(57) ABSTRACT

A stent comprising a serpentine portion extending about the circumference of the stent, the serpentine portion having a first end and a second end, the serpentine portion having a plurality of turns at the first end and a plurality of turns at the second end and struts extending therebetween, at least one of the turns at the first end, at least one of the turns at the second end, at least one of the struts therebetween, or some combination thereof having a plurality of shaped recesses thereon.

13 Claims, 25 Drawing Sheets

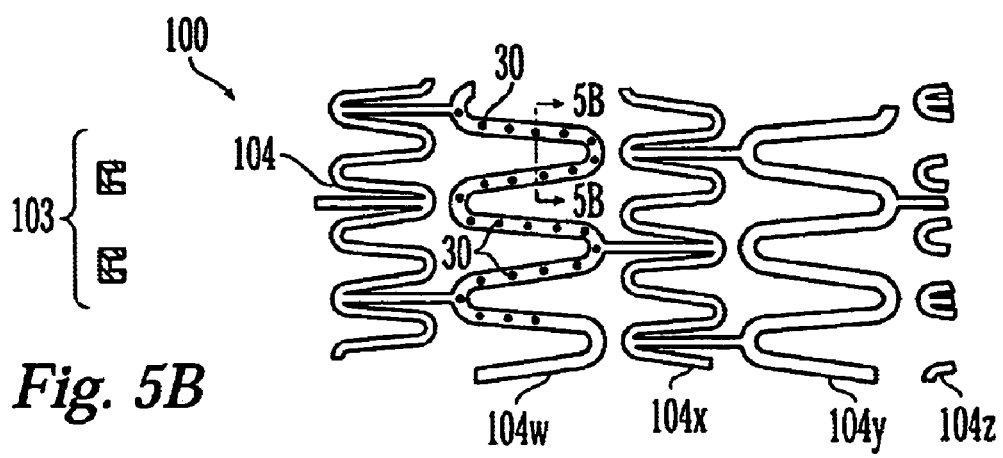
*Fig. 5B*
*Fig. 5A*
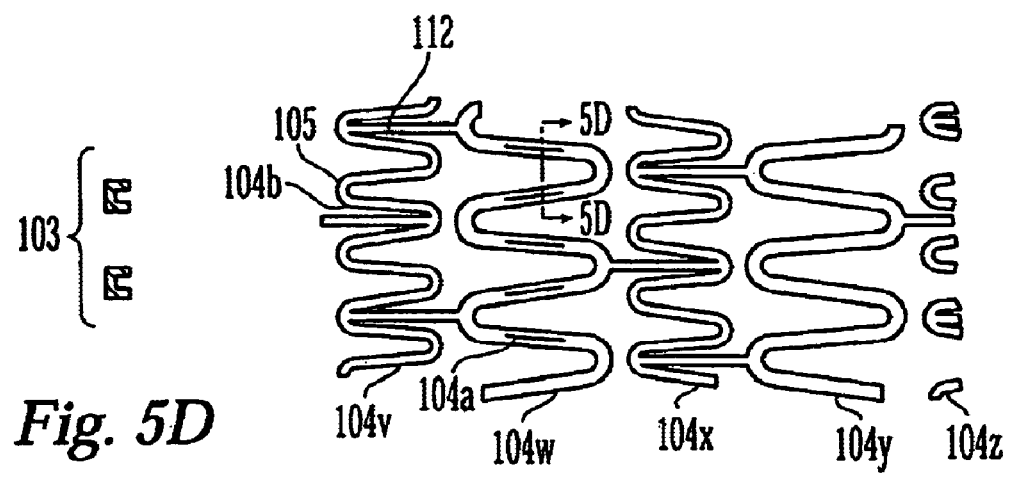
*Fig. 5D*
*Fig. 5C*

STENT DESIGNED FOR THE DELIVERY OF THERAPEUTIC SUBSTANCE OR OTHER AGENTS

FIELD OF THE INVENTION

The present invention relates to a system for delivering substances into a body.

BACKGROUND OF THE INVENTION

Stents are used for a variety of medical purposes in the body including in the coronary arteries, the peripheral arteries, arteries of the neck, cerebral arteries, veins, biliary ducts, urethras, ureters, fallopian tubes, bronchial tubes, the trachea, the esophagus and the prostate. Stents are typically placed or implanted within a bodily vessel, for example, for treating stenoses, strictures or aneurisms therein. They are implanted to reinforce collapsing, partially occluded, weakened, or dilated sections of a blood vessel.

Stents are typically available in self-expanding configuration and mechanically expandable configuration. Hybrid stents which are self-expanding in part and mechanically expandable in part are also available.

Many stents are manufactured with struts having a zig-zag or serpentine configuration which resembles that of a sine wave. An example of a serpentine portion of a stent is shown at 104 in FIG. 4a. Serpentine portion 104 extends about the circumference of the stent and includes a plurality of turns 105 which extend between adjacent struts. The individual struts are oriented at an angle $\Theta_1$ relative to longitudinal axis 101 of the stent. When a stent comprising one or more of serpentine portions 104 is radially expanded from an unexpanded state to an expanded state, as shown in FIG. 4b, the angle $\Theta_2$ of the struts increases relative to the longitudinal axis and the effective strut length decreases from L to L-ΔL resulting in foreshortening of the stent.

Foreshortening of stents during deployment, however, is undesirable, as it reduces the placement accuracy of the stent. There remains a need for innovative stents which do not foreshorten upon expansion.

Further, it is often desirable to deliver drugs into a patient's body to treat medical conditions. In particular, a variety of drug therapies are available for treating the coronary system, either alone or in combination with more invasive procedures. Such therapies may include delivering substances, such as nitroglycerin, epinephrin, or lidocaine, endocardially or into the pericardial space to treat the coronary system. In addition, heparin, hirudin, ReoPro® or other anti-thrombotic compounds may be infused into blood vessels associated with the coronary system, such as occluded coronary arteries, or elsewhere in the cardiovascular system. More recently, gene therapy, e.g. introducing genetic material, and growth factor therapy, e.g. introducing proteins, cells or vectors including angiogenic growth factors, have been demonstrated to provide potential benefits in treating ischemic heart tissue and other regions of the coronary system, for example, by stimulating growth of neovascular conduits, which may evolve into new blood vessels.

Various methods have been used to introduce drugs into the vasculature including, for instance, infusion catheters which may be optionally equipped with either a porous perfusion balloon, and/or with an electrode and/or heating element to improve localized delivery for continuous or intermittent delivery, ionophoresis in which a first electrode may be provided within a perfusion balloon, and a second electrode provided on an external region of the patient's body near the artery, embedding or depositing a drug on a catheter wall, a non-porous balloon wall on the catheter and/or a coating on the catheter, and so forth.

Another method of drug delivery has been to employ a stent. U.S. Pat. No. 6,258,121 describes, for example, a stent having a polymeric coating for controllably releasing an included active agent.

Without limiting the scope of the invention, a brief summary of the invention is set forth below. Additional details of the summarized embodiments of the invention and/or additional embodiments of the invention may be found in the Detailed Description of the Invention below.

BRIEF SUMMARY OF THE INVENTION

In one embodiment the present invention is directed to a stent having a strut with a first side and a second side, each side having alternating crests and troughs. The crests of the first side align with the troughs of the second side. The stent further has at least one adjacent strut which has a first side and a second side, each side having alternating crests and troughs. The crests of the first side of the adjacent strut align with the troughs of the second side of the adjacent strut. Furthermore, the crests of the first side of the first strut align with the crests of the second side of the adjacent strut and the troughs of the first side of the first strut align with the troughs of the second side of the adjacent strut.

In one embodiment, the struts have a wave-like pattern.

In another embodiment, the struts have at least one shaped recess between the crest of a first side and the trough of a second side which align. Preferably, each aligning crest of the first side and trough of the second side will have a shaped recess as will the adjacent struts. The shaped recesses may be used to hold therapeutic agents which are then delivered via the stent to the point of release. Desirably, shaped recesses may be located between every crest of the first side and trough of the second side of the strut, as well as on adjacent struts. This particular configuration allows for a maximum amount of drug delivery without sacrificing the strength of the stent.

The shaped recesses may be of any geometric shape or pattern and in some embodiments the shaped recesses are elongated ellipsoids or substantially circular shapes.

In another embodiment, the invention is directed to a stent comprising a serpentine portion extending about the circumference of the stent. The serpentine portion has a first end with a plurality of turns and a second end with a plurality of turns and struts extending therebetween. At least one of the turns at the first and second ends, and/or some of the struts of the serpentine portion have fully enclosed cut-out regions extending therethrough, and/or have shaped recesses which do not extend all the way therethrough, but rather which are enclosed on three sides and open on the top. The shaped recesses are smaller in dimension than either the turns or the struts.

Desirably, the stent comprises a plurality of serpentine portions extending about the circumference of the stent, each of which has a plurality of turns at the first and second ends. At least some of the turns at the first end and at the second end of each serpentine portion desirably have fully enclosed cut-out regions extending therethrough or shaped recesses which do not extend all the way therethrough. More desirably, each turn at each end of the serpentine portions has a cut-out region extending therethrough and/or a shaped recess which does not extend all the way therethrough.

The inventive state may be provided in an embodiment having a proximal serpentine portion at a proximal end of the stent and a distal serpentine portion at a distal end of the stent where at least one and desirably both of the proximal and distal serpentine portions have a plurality of turns with cut-out regions extending therethrough and/or shaped recesses thereon which do not extend all the way therethrough.

Some of the turns of the serpentine portions of the inventive stents may have cut-out regions and/or shaped recesses or all of the turns may have cut-out regions and/or shaped recesses. In one embodiment, every other turn has a cut-out region and/or shaped recess.

In some embodiments, some or all of the struts may have shaped recesses thereon. Each strut may have one or more shaped recess thereon. In some embodiments some of the turns at the first and/or second end may also have shaped recesses. Each turn may have only one, or may have a plurality of shaped recesses thereon.

In accordance with the invention, the cut-out regions and/or struts may assume a regular shape or an irregular shape.

In some embodiments of the invention, each turn having a cut-out region and/or shaped recess therein comprises an inner turn having a first width and an outer turn having a second width wider than the first width. The cut-out region and/or shaped recess disposed between the inner turn and the outer turn. In other embodiments of the invention, each turn having a cut-out region and/or shaped recess therein comprises an inner turn having a first width and an outer turn having a second width wider narrower than the first width. In yet other embodiment, the first width is equal to the second width.

The inventive stents disclosed herein may be provided in embodiments in which the number of cut-out regions and/or shaped recess per serpentine portion varies along the length of the stent. Desirably, at least one serpentine portion at one end and, more desirably, both ends of the stent will have more cut-out regions and/or shaped recesses than any of the serpentine portions in the intermediate section of the stent.

The inventive stents disclosed herein may also be provided in embodiments in which the size of the cut-out regions and/or shaped recesses in the serpentine portions varies along the length of the stent. Desirably, at least one serpentine portion at one end and, more desirably, both ends of the stent will have larger cut-out regions and/or shaped recesses than any of the serpentine portions in the intermediate section of the stent.

In some embodiments, the invention is directed to a radially expandable stent comprising a plurality of serpentine portions extending about the circumference of the stent, each serpentine portion having a plurality of turns where at least some of the turns have fully enclosed cut-out regions extending therethrough. The cut-out regions are distributed about the stent so that the stent opens in a non-uniform manner. In one embodiment, the stent includes a proximal serpentine portion at a proximal end of the stent, a distal serpentine portion at a distal end of the stent and a middle portion disposed between the proximal and distal ends of the stent and the cut-out regions are distributed such that one or both of the proximal and distal ends of the stent open prior to the middle portion of the stent. In another embodiment, the cut-out regions may be distributed such that the middle portion of the stent opens prior to one or both ends of the stent. The cut-out regions are typically substantially arcuate prior to expansion of the stent although other shaped cut-out regions may also be employed. Desirably, each turn of each serpentine portion has a cut-out region. Optionally, in these embodiments, shaped recesses for delivery of therapeutic agents may be provided in combination with cut-out regions providing a stent that opens in an non-uniform manner, and a stent that delivers a therapeutic substance.

The invention is further directed to a stent comprising at least one tubular serpentine member having a first end and a second end. The serpentine member has a plurality of turns at the first end and a plurality of turns at the second end amd struts extending therebetween. In some embodiments, each of the turns at the first and second ends have a fully enclosed cut-out region extending therethrough. In some embodiments, each of the turns of the first and second ends and/or the struts have shaped recesses thereon. Typically, the stent will comprise a plurality of tubular serpentine members with adjacent tubular serpentine members connected one to the other. Desirably, in those embodiments having fully enclosed cut-out regions, the shape of the fully enclosed cut-out regions changes as the stent is expanded. More desirably, the fully enclosed cut-out regions are characterized by a first area when the stent is in an unexpanded configuration and by a second area when the stent is in an expanded configuration, the second area larger than the first area.

The inventive stents may also be provided in embodiments in which the fully enclosed cut-out regions and/or shaped recesses are characterized by a first width when the stent is in an unexpanded configuration and by a second width when the stent is in an expanded configuration, the second width greater than the first width. Typically, the cut-out regions and/or shaped recesses of the inventive stents will be arcuate when the stent is in the unexpanded state although cut-out regions and/or shaped recesses of other shapes are also disclosed herein.

In another embodiment, the invention is directed to a stent comprising a serpentine portion extending about the circumference of the stent, the serpentine portion having a first end and a second end, the serpentine portion having a plurality of turns at the first end and a plurality of turns at the second end and struts extending therebetween, at least one of the turns at the first end, at least one of the turns at the second end, at least one of the struts therebetween, or some combination thereof have a plurality of shaped recesses thereon.

The shaped recesses may be of any geometry. In some embodiments, the shaped recesses are substantially circular, or are ellipsoids.

The invention is also directed to the combination of any of the inventive stent disclosed herein and a catheter. The stent has a proximal end and a distal end and a plurality of interconnected serpentine bands including a serpentine band having a plurality of cut-out regions and/or shaped recesses therein located on turns of the serpentine band or on the struts of the serpentine band. The stent is disposed about a portion of the catheter and the retaining sleeve disposed about one of the proximal and distal ends of the stent. The retaining sleeve is disposed about one or more serpentine bands having cut-out regions and/or shaped recesses. The catheter may optionally be provided with retaining sleeve at both the proximal and distal ends of the stent.

In some embodiments of the present invention, the stent is of a typical stent geometry having connectors and struts forming the framework of the stent. The stent framework further has shaped recesses which provide a reservoir for holding a substance or drug to be delivered within the body of a patient. The shaped recesses may be of various configurations or geometries, and may be of varying depth and size, i.e. width and length or circumference. Furthermore, the number of shaped recesses located in the framework of the stent may also be varied. In this embodiment, the stents are designed to deliver substances or drugs to target locations within a person's body. More particularly, in some embodiments the stent is designed to deliver substances or drugs within the vasculature of a patient such as therapeutic agents including, but not limited to, genetic material, growth factors, antineoplastics, antimitotics, anti-inflammatories, antiplatelets, anticoagulants, antifibrins, antithrombins, antiproliferatives, antibiotics, antioxidants, and antiallergenic substances, and so on and so forth, as well as combinations thereof. The present invention allows the substances to be deposited directly at targeted locations within the body or directly to selected tissue regions within the body.

The stents of the present invention may therefore have cut-outs, shaped recesses, or some combination thereof, within the framework of the stents.

Additional details and/or embodiments of the invention are discussed below.

BRIEF DESCRIPTION OF THE DRAWING(S)

FIG. 3a is an alternative embodiment of the stent portion as shown in FIG. 2a.

FIG. 5a shows an inventive stent having shaped recesses in the flat.

FIG. 5b is a sideview of a recess of FIG. 5a.

FIG. 5c shows an inventive stent having alternative shaped recesses in the flat.

FIG. 5d is a sideview of a recess of FIG. 5c.

FIGS. 8a–10a show a portion of a serpentine portion of a stent in an unexpanded state, an expanded state and a crimped state, respectively.

FIGS. 8b–10b represent the same stent configuration as that in FIGS. 5a–7a but with shaped recesses.

FIGS. 8c–10c represent the same stent configuration as that in FIGS. 5a–7a but with alternative shaped recesses.

Figure 11A:
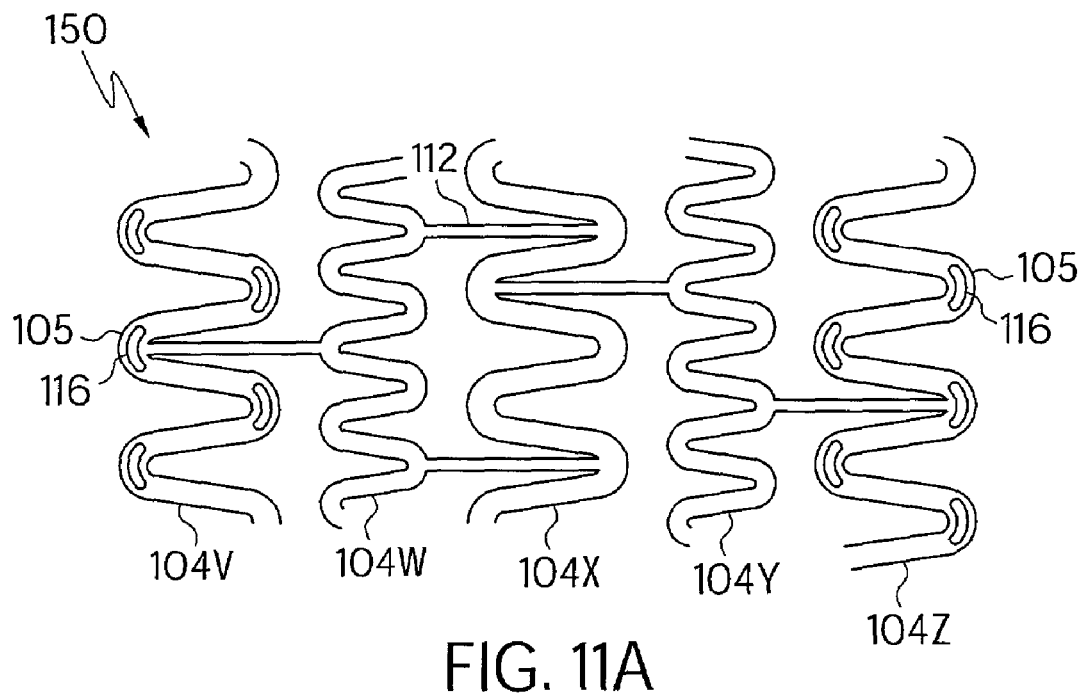
FIGS. 11a–11c and 12 show other inventive stents in the flat.
Figure 11B:
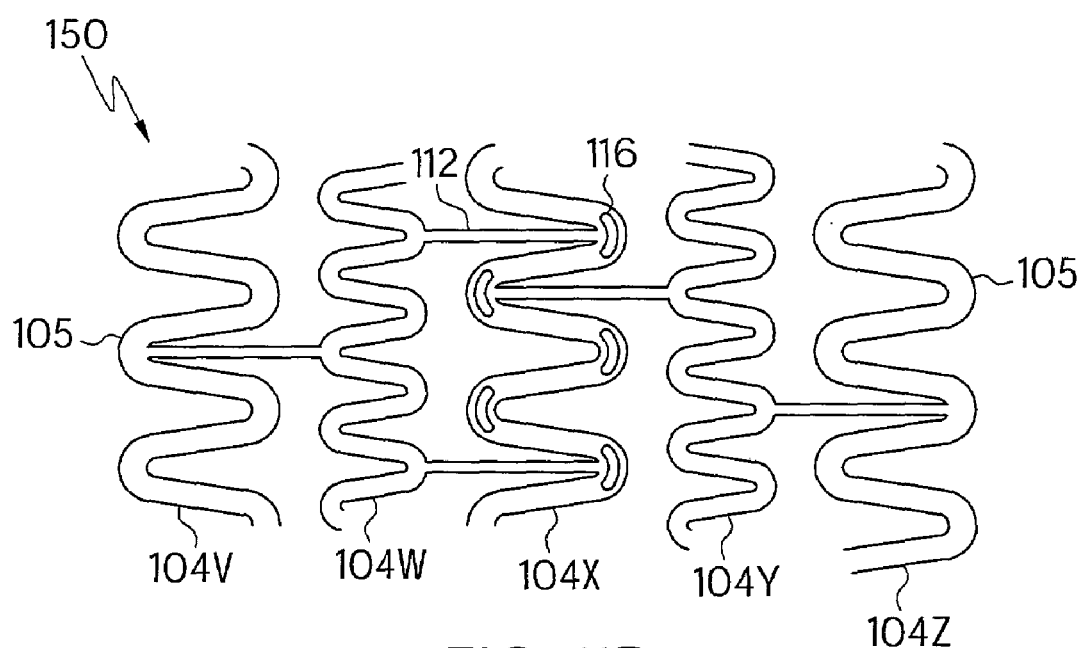
Figure 11C:
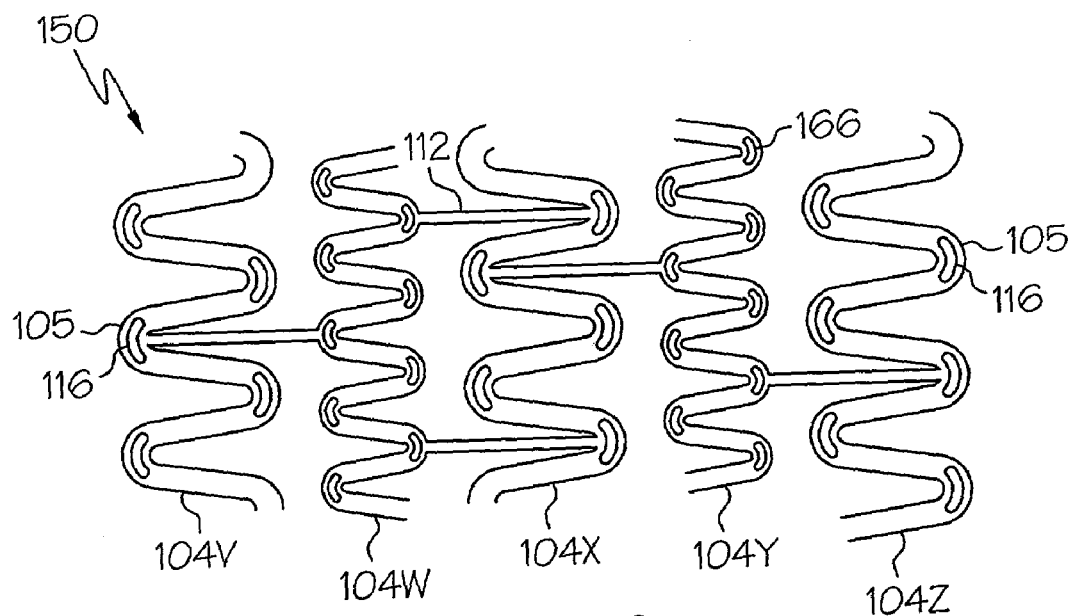
Figure 11D:
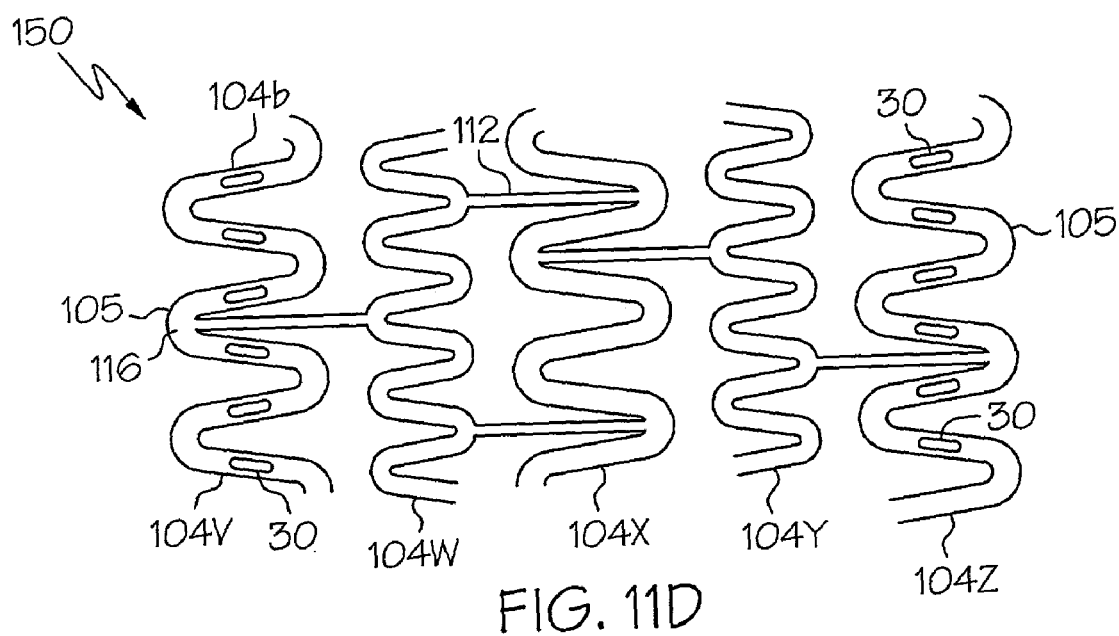
Figure 11E:
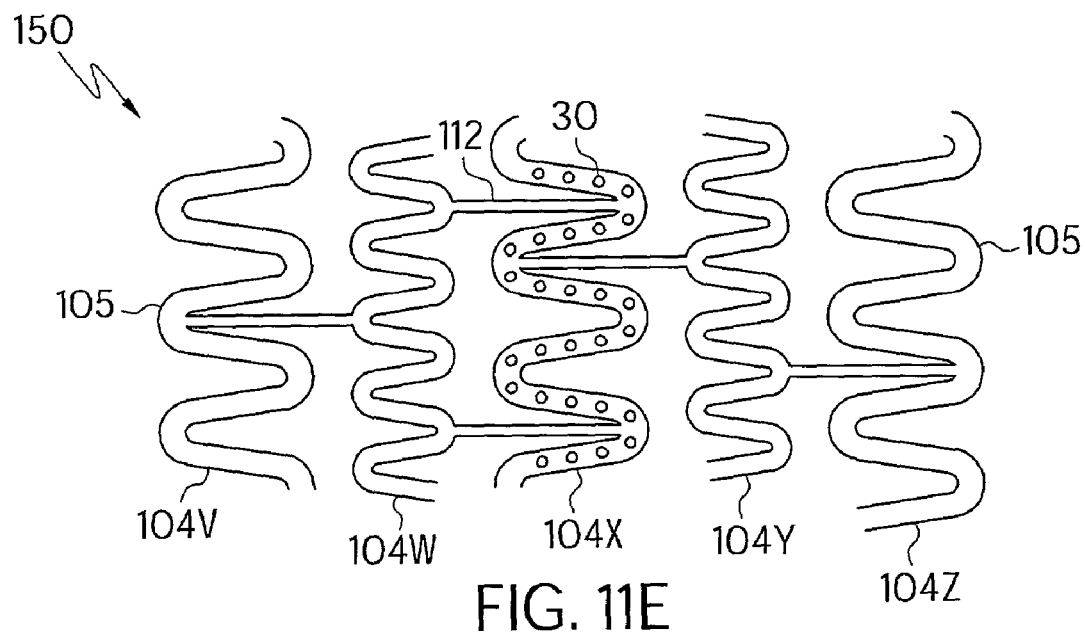
Figure 11F:
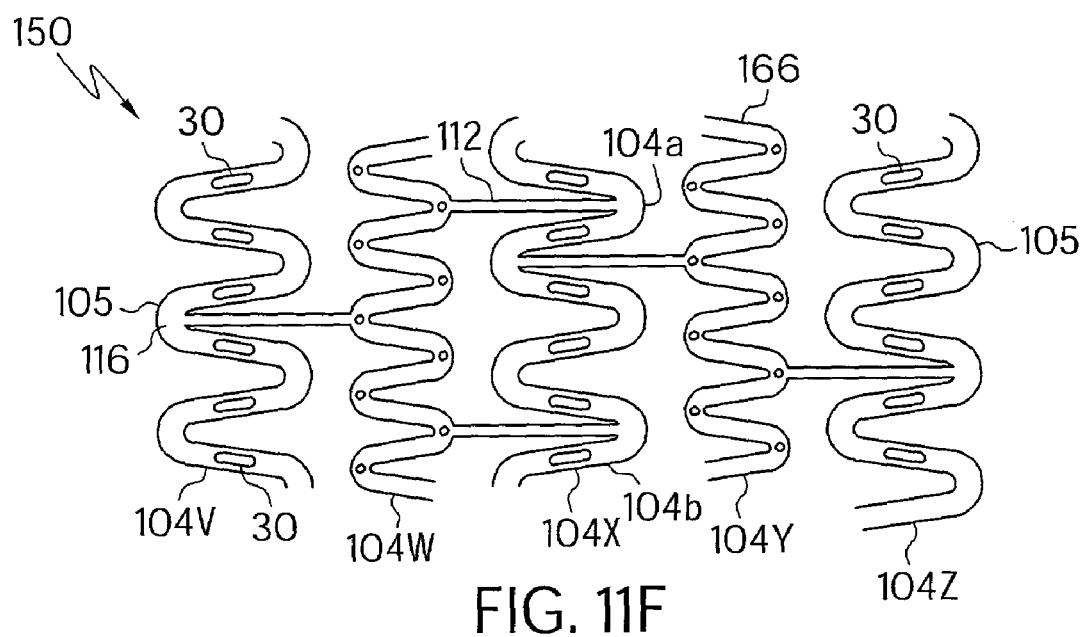

FIGS. 11d–11f shown alternative embodiments of the stents shown in FIGS. 11a–11c.

Figure 11G:
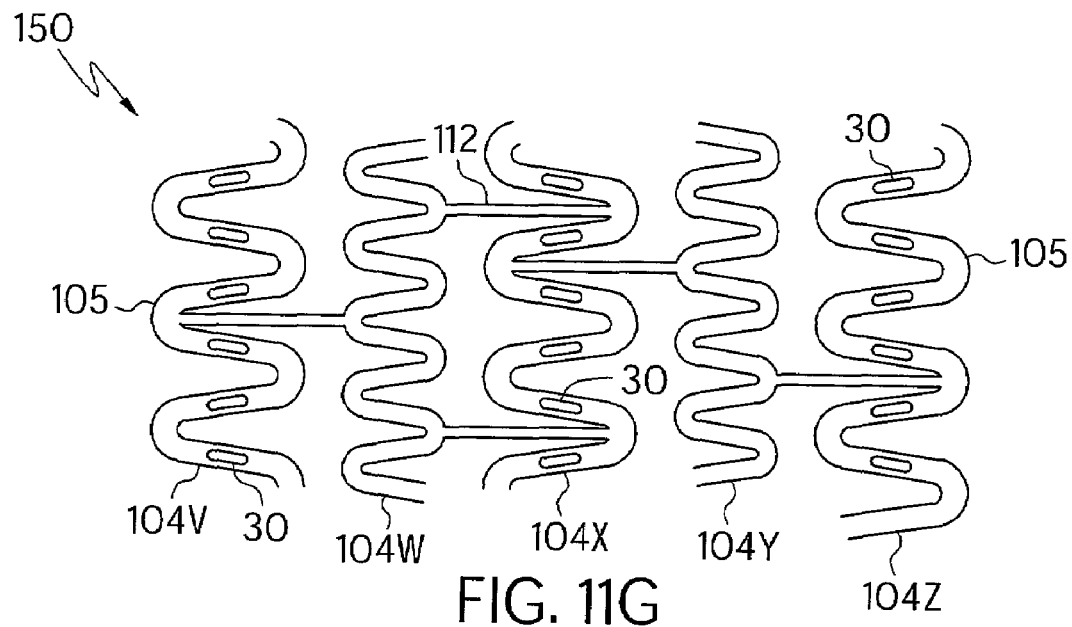
Figure 11H:
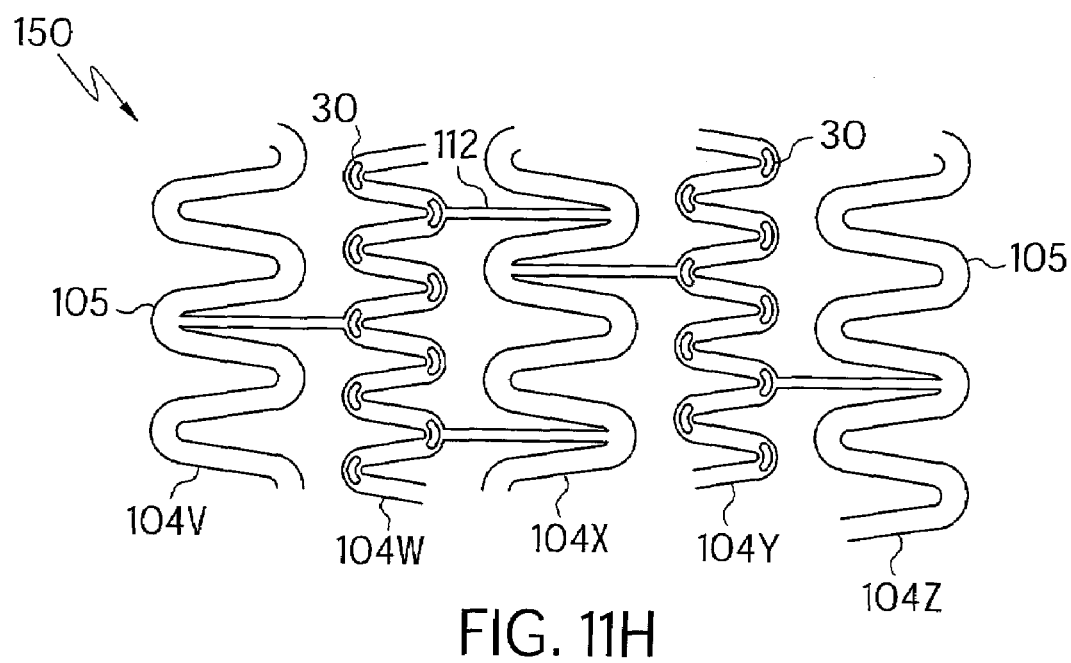
Figure 11I:
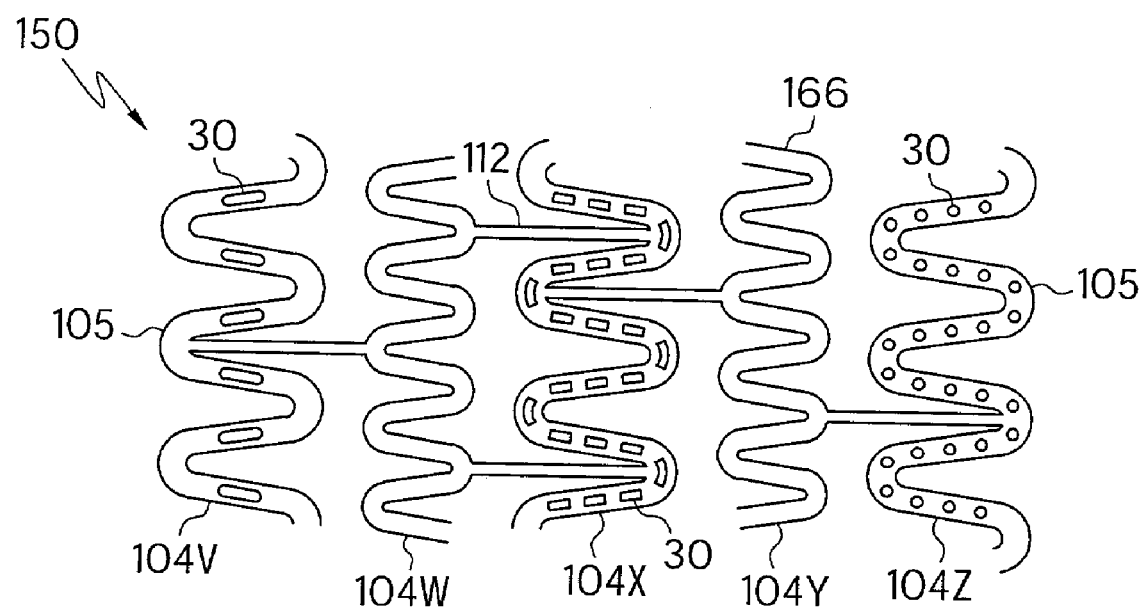

FIGS. 11g–11i show yet other embodiments of the stents of FIGS. 8a–8f.

FIGS. 13–23 show other configurations of cut-out regions and/or optionally shaped recesses.

Figure 24:
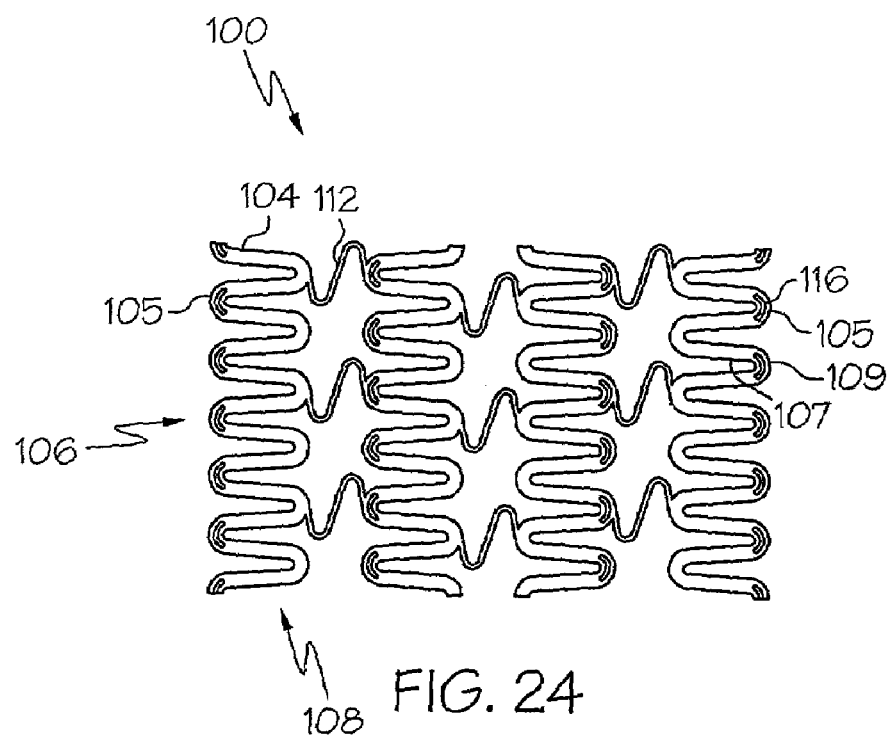
Figure 25:
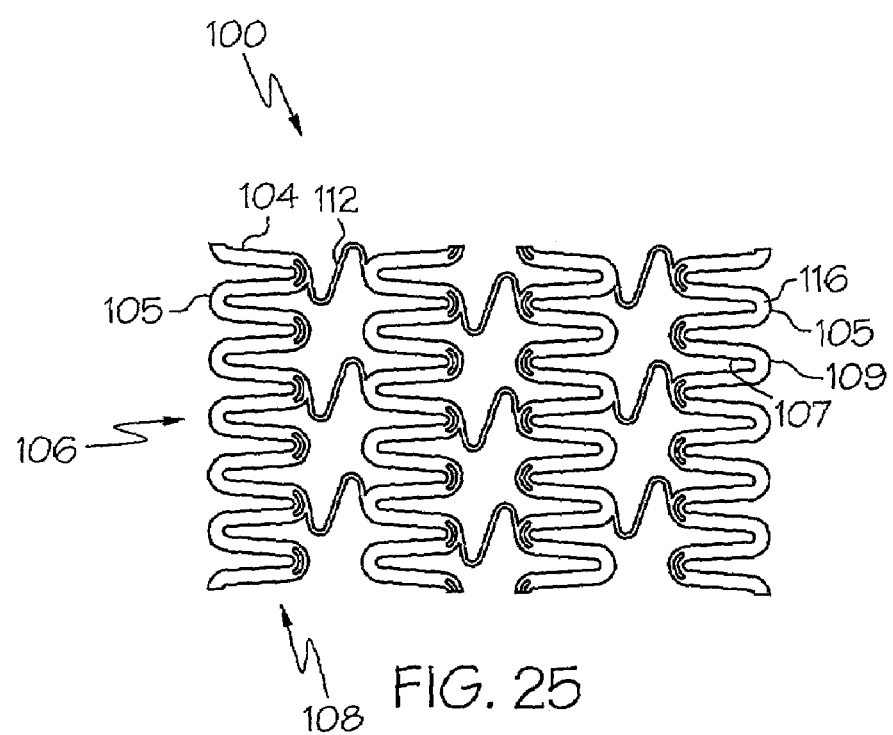
Figure 26:
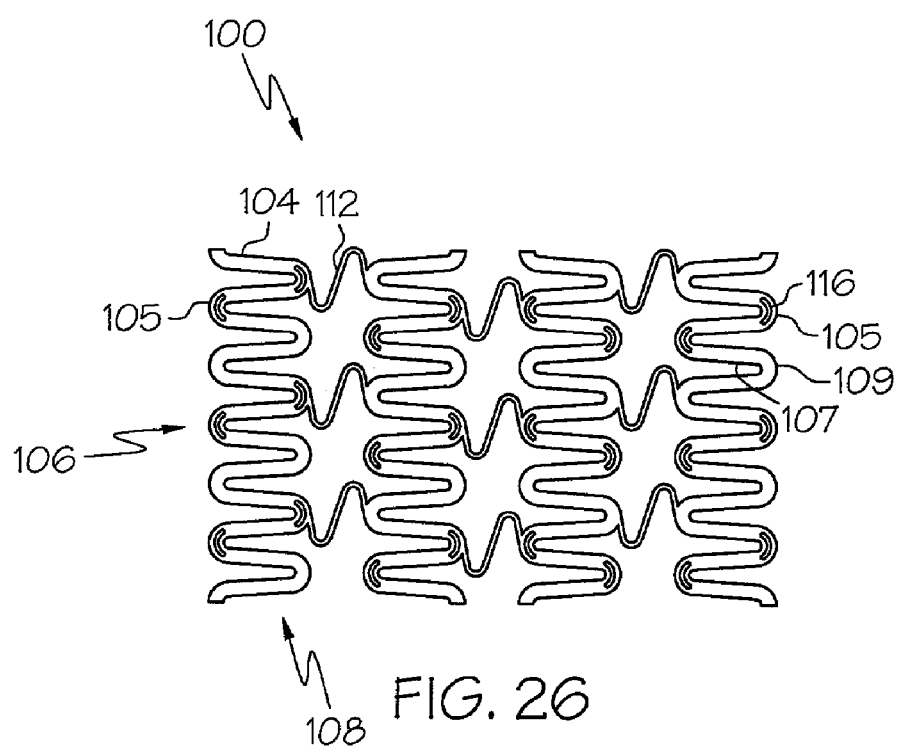

FIGS. 24–26 show other inventive stents in the flat.

Figure 27:
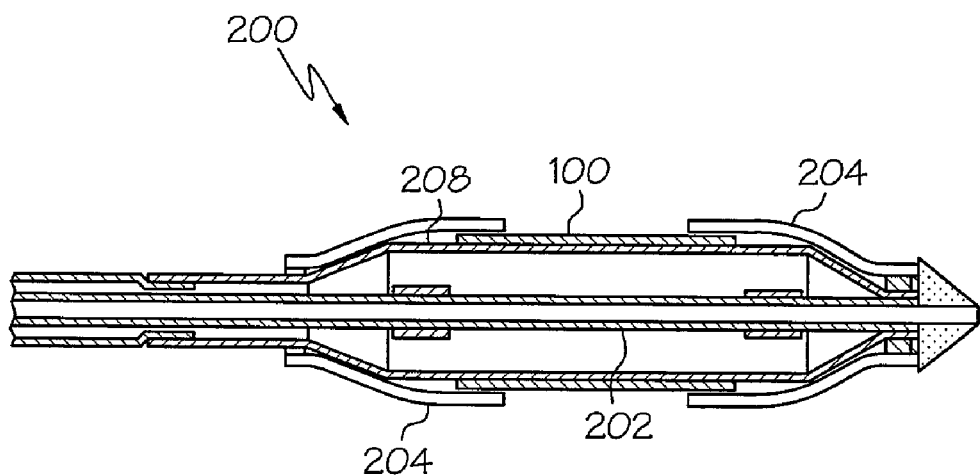

FIG. 27 shows an inventive combination of a catheter and a stent with cut-out regions and/or optionally shaped recesses.

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated. Also for the purposes of this disclosure, the term "cut-out region" shall refer to a region of a serpentine portion of a stent having an opening therethrough, the opening surrounded by stent material. The term does not imply any particular method of forming a stent with cut-outs but, rather, refers to the absence of stent material in the region of the cut-out.

Further, for purposes of this disclosure, the term "shaped recess" shall refer to a region of a serpentine portion of a stent which does not have an opening therethrough, but rather is a recess in the stent material of varying depth. The term shaped recess shall be used hereinafter to encompass those regions of the serpentine portion of a stent which are reservoirs which may be employed to hold substances such as therapeutic agents and which term may also be used to encompass those which could be described as grooves, channels, slits, flutes, trenches, holes, and so on and so forth. The shaped recess may be of any geometry. Some particular geometries include elongated ellipsoids, substantially circular recesses, oval, rectangular, square, triangular, and so on and so forth. Hereinafter, the term "substantially circular" shall be used to include oval and so forth.

These shaped recesses are regions of the serpentine portion of a stent which are of varying depths and which do not extend all the way therethrough. The term "stent material" as used above does not refer to any therapeutic agent which might be provided in the cut-out or shaped recess of the present invention.

In general, this invention provides a radially expandable stent formed of any appropriate stent material including the shape memory alloys such as the nickel-titanium shape memory alloys, for example NITINOL®, or stainless steel, for example. The stent includes a series of struts which act as circumferential segments circumscribing the cylindrical contour of the stent. Each strut is alighend with a separate plane perpendicular to a central axis of the cylindrical contour of the stent and parallel to other planes to which adjacent struts are aligned. The stent can have various different numbers of struts joined together to form the stent.

In one particular embodiment of the present invention, each strut has a first side and a second side and each side has a series of bends which have troughs and crests alternating along the length of each strut. The crests of the first side of each strut align with the troughs of the second side of each strut.

The struts may be adjacent to one another. Each adjacent strut has a first side and a second side, each side having a series of bends which have troughs and crests alternating along the length of each strut. A trough of the first side of a strut will align with a trough of the second side of an adjacent strut and a crest of the first side of a strut will align with a crest of the second side of an adjacent strut.

The amplitude of each strut may be varied. Furthermore, the amplitude from strut to strut may be varied as well. The amplitude is defined by the distance between the bottom of each trough and the top of each crest and is modified when the stent is radially expanded and the amplitude is decreased.

Longitudinally adjacent struts may be connected to one another through connecting members. In various embodiments, the members are substantially linear, ushaped, v-shaped, s-shaped and so forth.

Figure 1A:
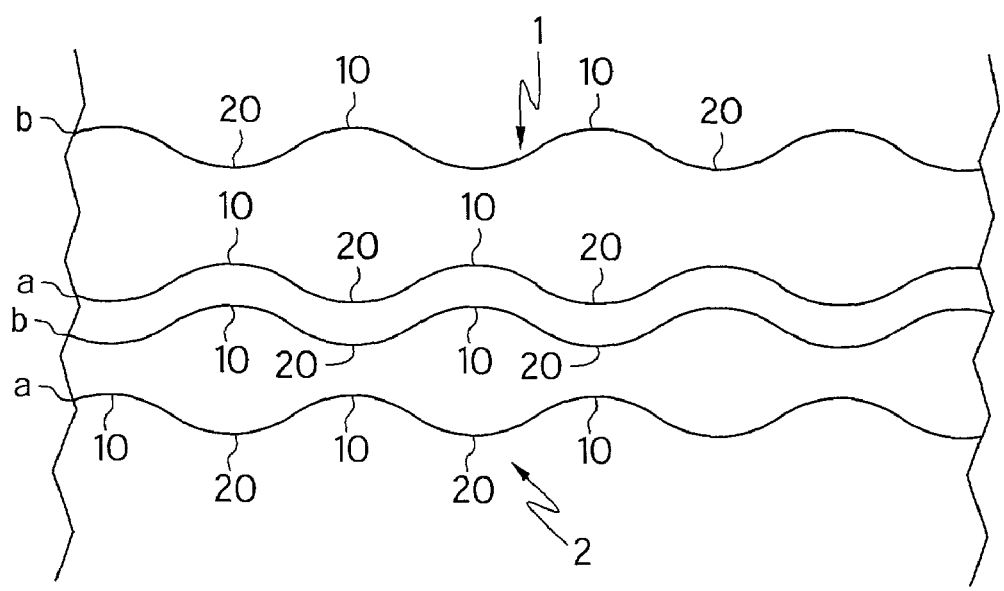
FIG. 1a is a detail of a portion of a stent showing an embodiment of the strut configuration of the present invention.

Turning now to the figures, FIG. 1a illustrates an embodiment of the present invention. Strut 1 has first side a and second side b and strut 2 has a first side a and a second side b. Additionally, each strut has crests 10 and troughs 20. The crests 10 of first side a of strut 1 align with the troughs 20 of second side b of strut 1. The crests of second side b of adjacent strut 2 align with the crests 10 of first side a of strut 1 and the troughs 20 of second side b of adjacent strut 2 align with the troughs 20 of first side a of adjacent strut 2. The amplitude as noted above, may be varied.

Figure 1B:
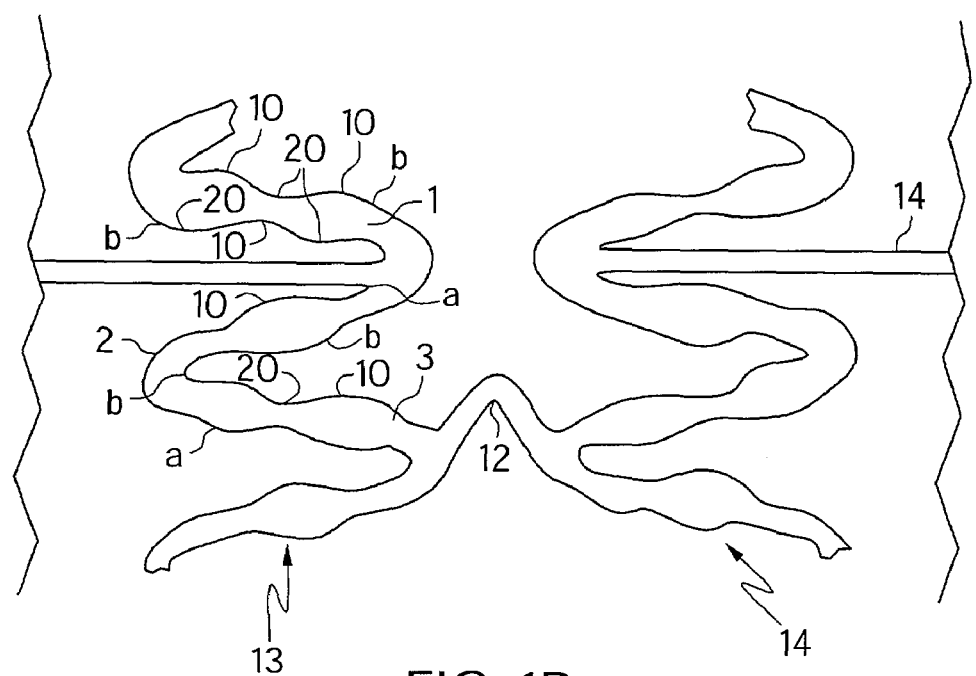
FIG. 1b is the same detail of a portion of the stent in FIG. 1a in an expanded state.

FIG. 1b illustrates the stent of FIG. 1a in an expanded state. Additionally, connecting members 12 and 14 are shown between longitudinally adjacent struts.

Figure 1C:
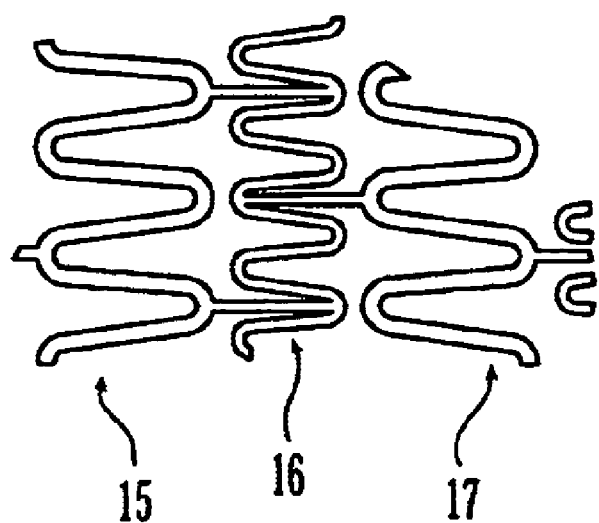
FIG. 1c shows a portion of a stent having struts that do not include the crests and troughs of the struts shown in FIGS. 1a and 1b.
Figure 1D:
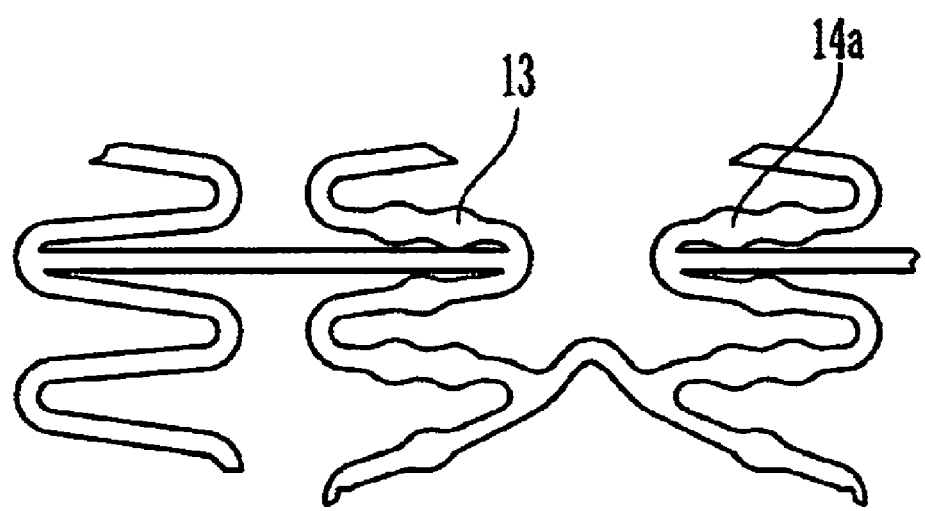
FIG. 1d shows the stent of FIG. 1c having its struts replaced by the struts of the stent shown in FIGS. 1a and 1b.

FIG. 1c illustrates a different type of strut configuration in which bands 15 and 17, for example, may be replaced with bands 13 and 14a of the present invention, as shown in FIG. 1d. Band 16 may also be replaced with the innovative strut pattern of the present invention. Furthermore, any combination of bands 15, 16, and/or 17 may be replaced with the strut pattern as described by the present invention.

Figure 2A:
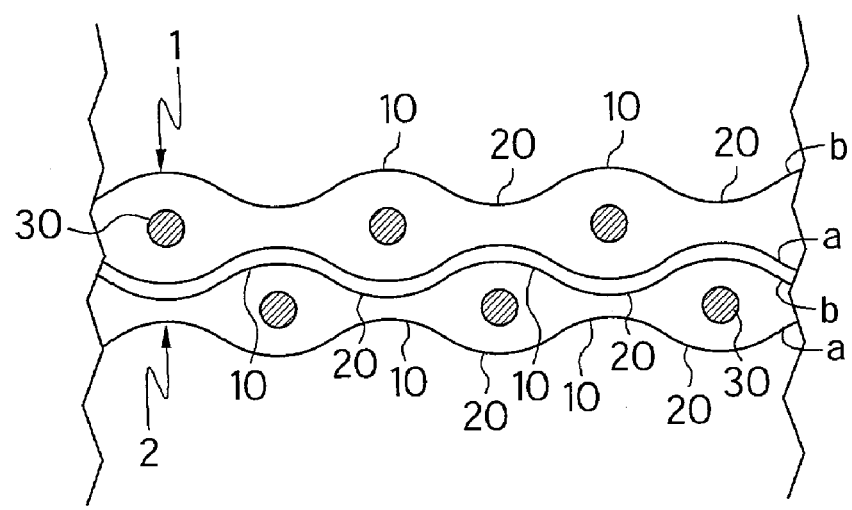
FIG. 2a is an alternative embodiment of a detail of a portion of a stent similar to that in FIG. 1a having shaped recesses thereon.

FIG. 2a illustrates an alternative embodiment of the present invention in which substantially circular shaped recesses 30 are located between the aligned crests 10 and troughs 20 on each strut 1,2. The shaped recesses 30 are suitably employed for containing therapeutic agents according to the present invention.

The quantity of the recesses employed on the stent, the size of the recess, and the depth, may all be varied in order to control the amount of a substance that is deposited into the body. The recesses assist in preventing the substance from being disturbed during crimping, and all allow delivery of the substance to a target location without removal of the substance because it is located at a subsurface.

The above described embodiment results in a stent structure wherein the recesses are in a staggered pattern from strut to strut. This particular embodiment is desirable because it allows the maximization of the surface area available for drug delivery, but without sacrificing the integrity of the stent itself.

Substances which may be delivered in this fashion may include any drugs or substances which are desirably delivered into the body of a patient, particularly those which it may be desirable to deliver at a target location in the body. Examples of such substances include, but are not limited to, therapeutic agents including drugs and radioactive materials. The term "therapeutic agents" as used herein includes, but is not limited to, antithrombins; antiproliferatives; anesthetics; antifibrins, anticoagulants; antineoplastic/antiproliferative/antimiotic agents; vascular cell growth promoters (i.e. proteins, cells or vectors including angiogenic growth factors) including growth factor promoters, transcriptional activators and translational promoters; vascular cell growth inhibitors including growth factor inhibitors, growth factor receptor antagonists, transcriptional repressors, translational repressors, replication inhibitors, inhibitory antibodies, antibodies directed against growth factors, bifunctional molecules consisting of growth factor and cytotoxin, and bifunctional molecules consisting of an antibody and a cytotoxin; cholesterol lowering agents; vasodilators; genetic material for gene therapy; platelet receptor antagonists; antiplatelet agents such as antiplatelet receptor antibodies; prostaglandin inhibitors; platelet inhibitors; tick antiplatelet peptides, antibodies; agents which interfere with endogenous vasoactive mechanisms; and so on and so forth.

Examples of antithrombins, anticoagulants, antiplatelets and antifibrins include, but are not limited to, thrombin inhibitors such as ANGIOMAX® from Biogen, Inc. in Cambridge, Mass.; D-phe-pro-arg-chloromethylketone (synthetic antithrombin); dextran; prostacyclin and prostacyclin analogues; sodium heparin; heparin and heparin derivatives; heparinoids; hirudin and recombinant hirudin; glycoprotein IIb/IIIa platelet membrane receptor antagonist antibody; prostacyclin and prostacyclin analogues; argatroban; forskolin; vapiprost; dipyridamole; urokinase, and PPack (dextrophenylalanine proline arginine cloromethylketone); RGC peptide-containing compound; platelet receptor antagonists; antithrombin antibodies; antiplatelet receptors; antibodies; aspirin; prostaglandin inhibitors; platelet inhibitors; tick antiplatelet peptides; and so forth.

Examples of cytostatic or antiproliferative agents include, but are not limited to, enoxaprin, angiopeptin, angiotensin converting enzyme inhibitors such as captopril including CAPOTEN® and CAPOZIDE® available from Bristol-Myers Squibb Co.; cilazapril or lisinopril such as PRINIVIL® and PRINIZIDE® available from Merck & Col. Inc. in Whitehouse Station, N.J.; calcium channel blockers such as nifedipine; colchicine; monoclonal antibodies capable of block smooth muscle cell proliferation, hirudin and recombinant hirudin, acetylsalicylic acid; fibroblast growth factor (FGF) antagonists; fish oil (omega 3-fatty acid); histamine antagonists; lovastatin (an inhibitor of antifibrin and an inhibitor of HMG-CoA reductase which is a cholesterol lowering drug available under the tradename of MEVACOR® from Merck & Co. Inc.); the antithrombins including sodium heparin, heparins and heparin derivatives, heparinoids, hirudin and recombinant hirudin, argatroban, forskolin, vapiprost, prostacyclin and prostacyclin analogues, dextran, dipyrimadole, D-phe-pro-arg-chloromethylketone (synthetic antithrombin), glcyoprotein IIb/IIIa platelet membrane receptor antagonist antibody, and so forth; thrombin inhibitors such as ANGIOMAX® from Biogen, Inc.; prostaglandin inhibitor; serotonin blockers; steroids; thioprotease inhibitors; PDGF antagonists; nitric oxide; monoclonal antibodies such as those specific for Platelet-Derived Growth Factor (PDGF) receptors; nitroprusside; phosphodiesterase inhibitors; suramin; serotonin blockers; triazolopyrimidine (a PDGF antagonist); and so forth.

Examples of anti-inflammatory agents include, but are not limited to, dexamethasone, prednisolone, corticosterone, budesonide, estrogen, sulfasalazine, mesalamine, and so forth.

Examples of antineoplastic/antiproliferative/antimiotic agents include, but are not limited to, paclitaxel such as TAXOL® Bristol-Myers Squibb Co. in Stamford, Conn.; docetaxel such as TAXOTERE® from Aventis S.A. in Frankfurt, Germany; methotrexate; azathioprine; vincristine; vinblastine; 5-fluorouracil; doxorubicin hydrochloride such as ADRIAMYCIN® from Pharmacia & Upjohn in Peapack, N.J.; mitomycin such as MUTAMYCIN® from Bristol-Myers Squibb Co. in Stamford, Conn.; cisplatin; epothilones; endostatin; angiostatin; thymidine kinase inhibitors; and so forth.

Examples of anesthetic agents include, but are not limited to, lidocaine, bupivacaine, ropivacaine, and so forth. An example of an antiallergenic agent is permirolast potassium. Another example of a therapeutic agent includes, but is not limited to, alpha-interferon.

Examples of genetic materials which may be deposited into a patient's body employing the stents of the present invention include, but are not limited to, anti-sense DNA and RNA, and DNA coding for tRNA and rRNA, cell cycle inhibitors including CD inhibitors, thymidine kinase (TK) and other agents useful for interfering with cell proliferation, bone morphogenic proteins (BMPs), and so forth.

Specific BMPs include, but are not limited to BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, BMP-16, and so forth. Preferred for use are BMP-2, BMP-3, BMP-4, BMP-5, BMP-6 and BMP-7. These dimeric proteins may be provided as homodimers, heterodimers, or combinations thereof, and alone or in combination with other molecules such as those molecules capable of inducing an upstream or downstream effect on a BMP. For example, "hedgehog" proteins or the DNA's which encode them may be employed in combination with the BMPs.

Cells which may be deposited at a target site in a body may be of human origin (autologous or allogeneic) or may be from an animal source (xenogeneic), or they may be genetically engineered if so desired to deliver proteins of interest at the transplant site such as epithelial cells. The delivery media may be formulated as needed to maintain cell function and viability as is known to those of skill in the art.

Radioactive isotopes may also be used for prosthesis usage in radiotherapeutic procedures and include, but are not limited to, phosphoric acid ($H_3P_{32}O_4$), palladium ($Pd^{103}$), cesium ($Cs^{131}$), iodine ($I^{125}$), and so forth.

The above lists are not exclusive and are intended for exemplary purposes only. The preventative and treatment properties of therapeutic substances or other agents are well known to those of ordinary skill in the art and as such, the above lists are simply provided by way of example, and are not intended to limit the scope of the present invention. Other therapeutic substances or other agents which are not listed herein are equally applicable for use and are also known to those of skill in the art.

Figure 2B:
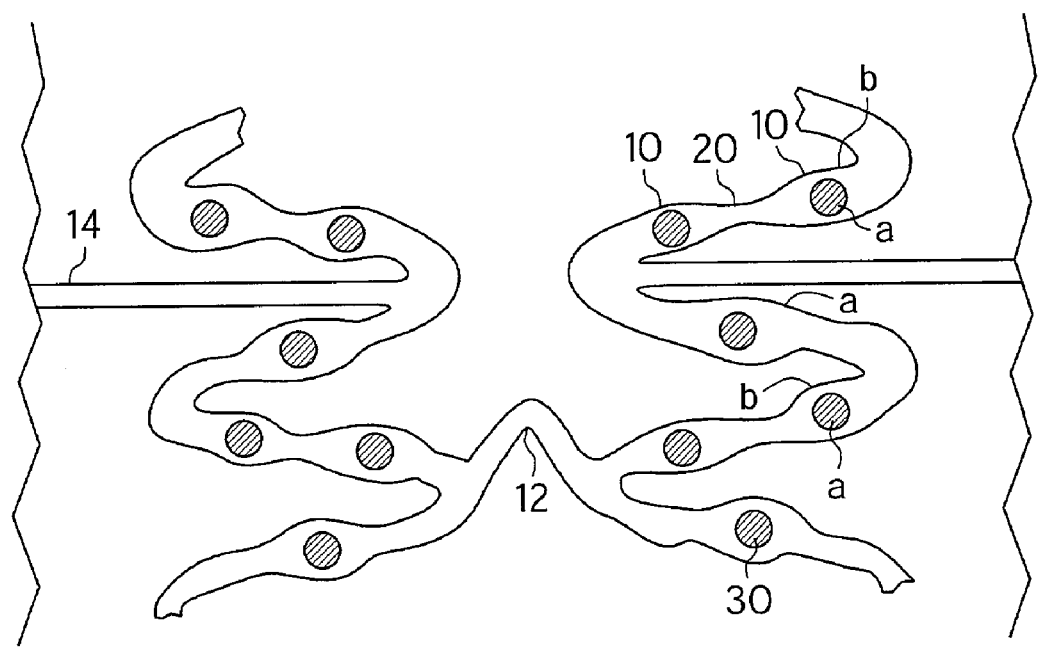
FIG. 2b is a detail of a portion of the stent structure as shown in FIG. 2a in an expanded state.

FIG. 2b shows the same stent configuration of FIG. 2a having the substantially circular shaped recesses 30 located between aligned crests 10 and troughs 20 on each strut 1, 2 in an expanded state.

Figure 3A:
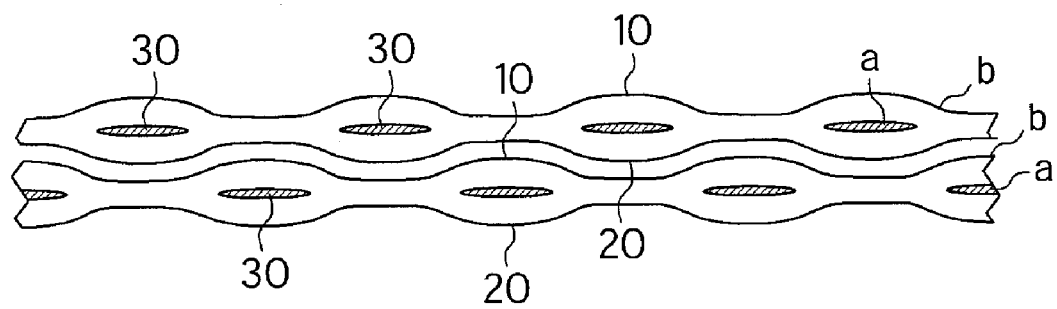
Figure 3B:
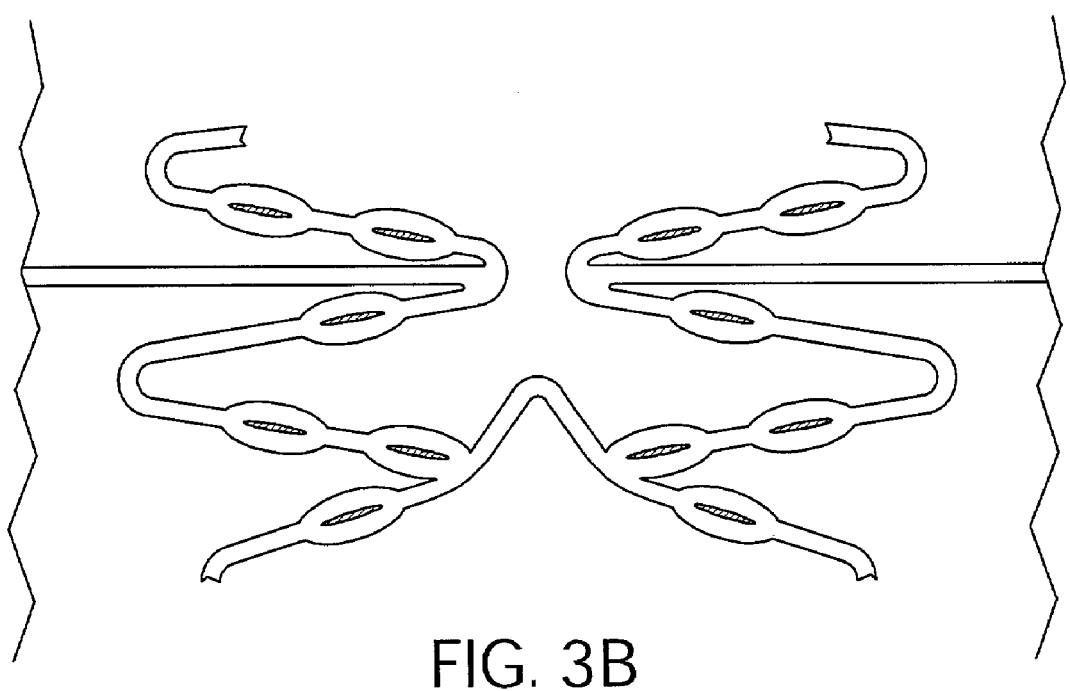
FIG. 3b is the stent structure of FIG. 3a shown in an expanded state.
Figure 4A:
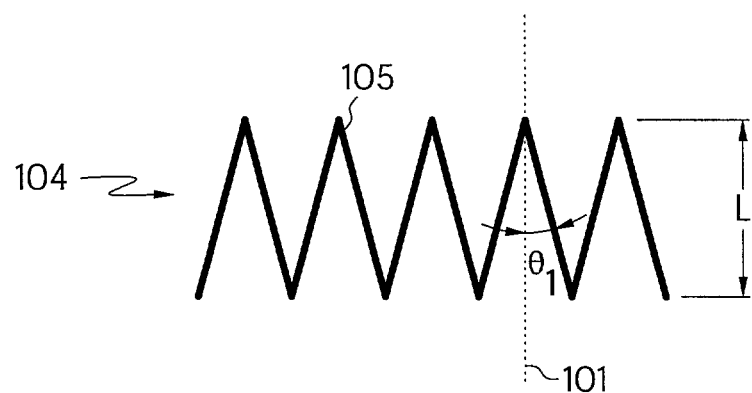
FIG. 4a shows a schematic representation of a serpentine band prior to expansion.
Figure 4B:
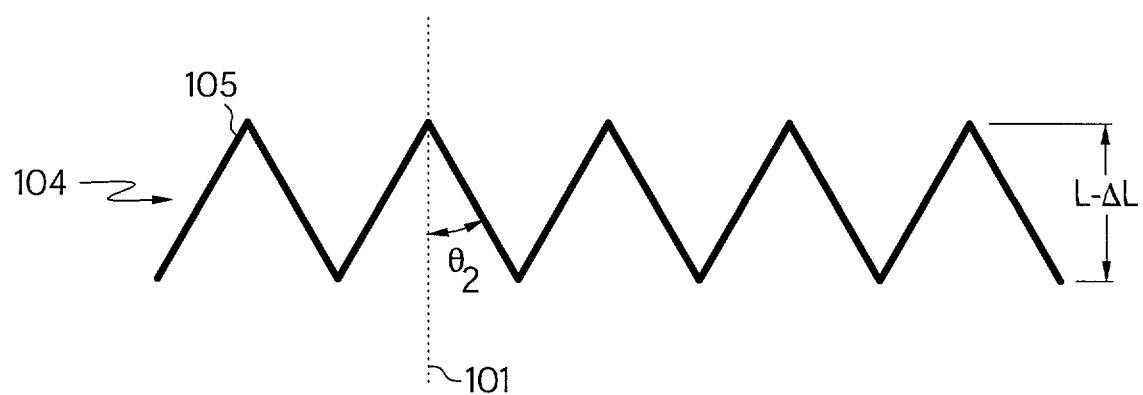
FIG. 4b shows a schematic representation of the serpentine band of FIG. 4a following expansion.

FIG. 3a illustrates an alternative embodiment of the stent configuration described in FIG. 2a in which the shaped recesses 30 are elongated ellipsoids. FIG. 3b illustrates the same stent configuration in an expanded state.

In another embodiment of the present invention, the stent may comprise a plurality of serpentine portions which extend about the circumference of the stent. For purposes of this disclosure, the term serpentine encompasses, but is not limited to, zigzag. Thus, a serpentine pattern encompasses, but is not limited to a pattern having sharp turns and a pattern having gradual turns.

Figure 6A:
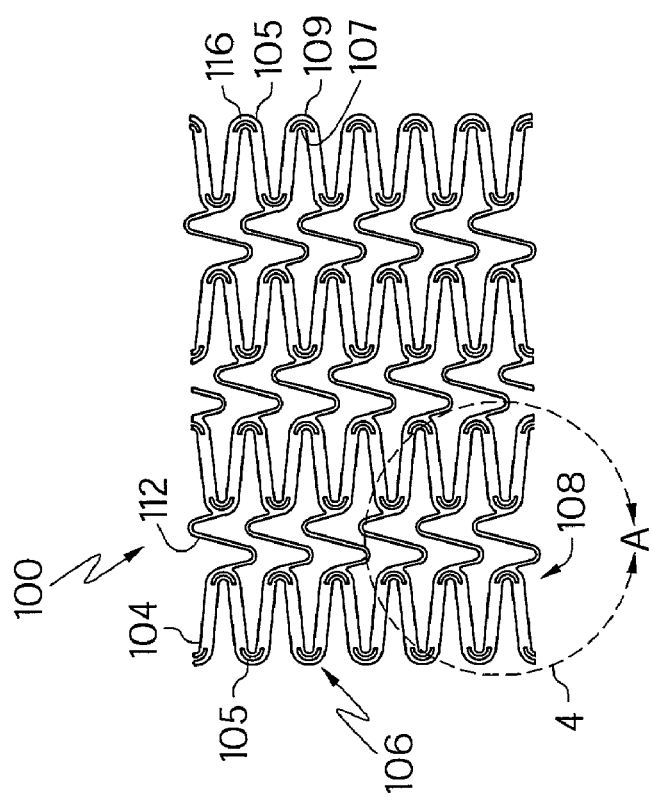
FIGS. 6a–6c shows an inventive stent having cut-outs in the flat.
Figure 7A:
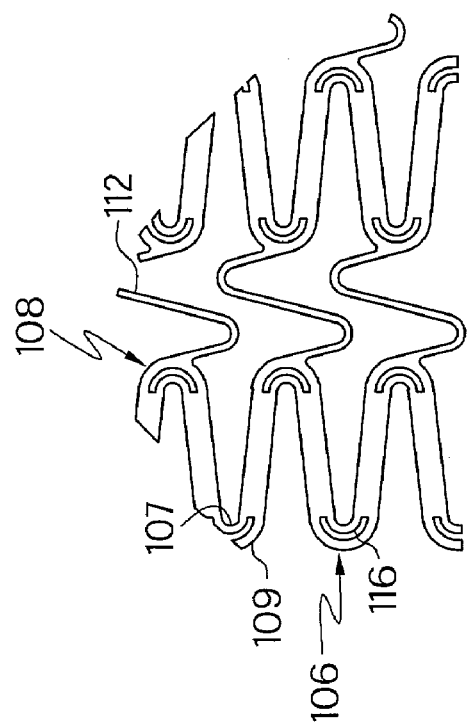
FIGS. 7a–7c are enlargements of the circled region 4 of the stents shown in FIGS. 6a–6c.

With reference to the figures, a stent comprising a plurality of serpentine portions which extend about the circumference of the stent is shown generally at 100 in FIG. 6a. Serpentine portions 104 include a plurality of turns 105 at the proximal and distal ends of the serpentine portions.

Serpentine portions 104 are connected one to the other via one or more connectors 112. As shown in FIG. 6a, connectors 112 include curved sections and struts. As used herein, the term "strut" shall be used to encompass both those struts which are straight in configuration, as well as those having any other configuration including those which are curvilinear. First end 112a and second end 112b of connectors 112 are circumferentially offset from one another.

As shown in FIGS. 6a–8a, proximal end 106 of serpentine portions 104 and distal end 108 of serpentine portions 104 are provided with cut-out regions 116. Typically, as shown in the figures, each turn at each end of each serpentine portion will be provided with a cut-out region. Cut-out regions 116 have substantially the same curvature as the turns 105 of the bands themselves and define an inner turn 107 and an outer turn 109. Desirably, cut-out region 116 extends substantially along a radius of turn 105.

Figure 8A:
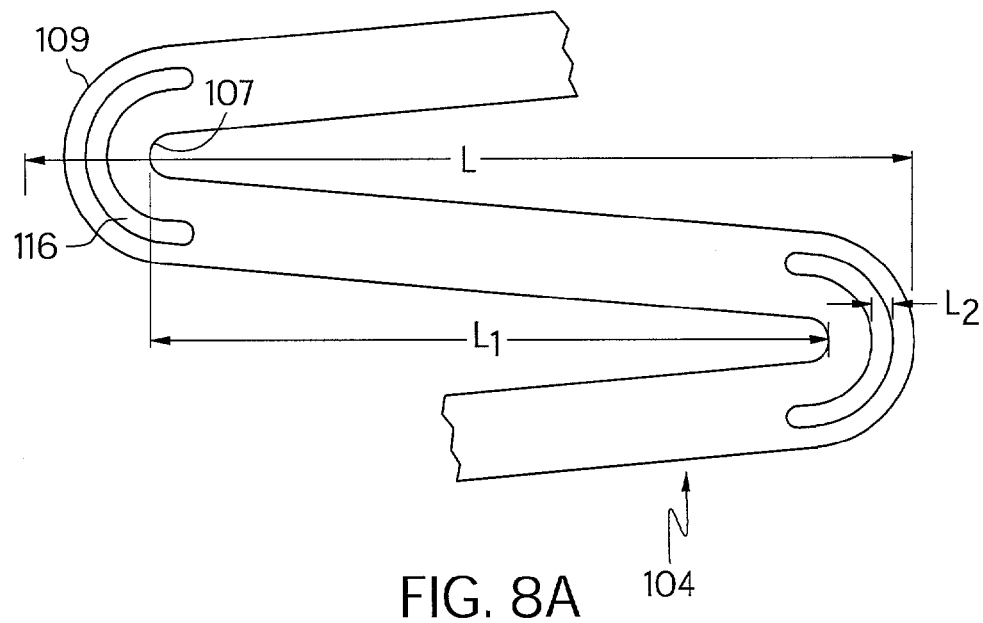

As shown in FIG. 8a, the total longitudinal length of serpentine portion 104 is denoted by L and the longitudinal separation between the inner radii of the serpentine portion is denoted by $L_1$. The width of the cut-out portion, as defined by the maximum separation between inner turn 107 and outer turn 109, is denoted by $L_2$.

Figure 9A:
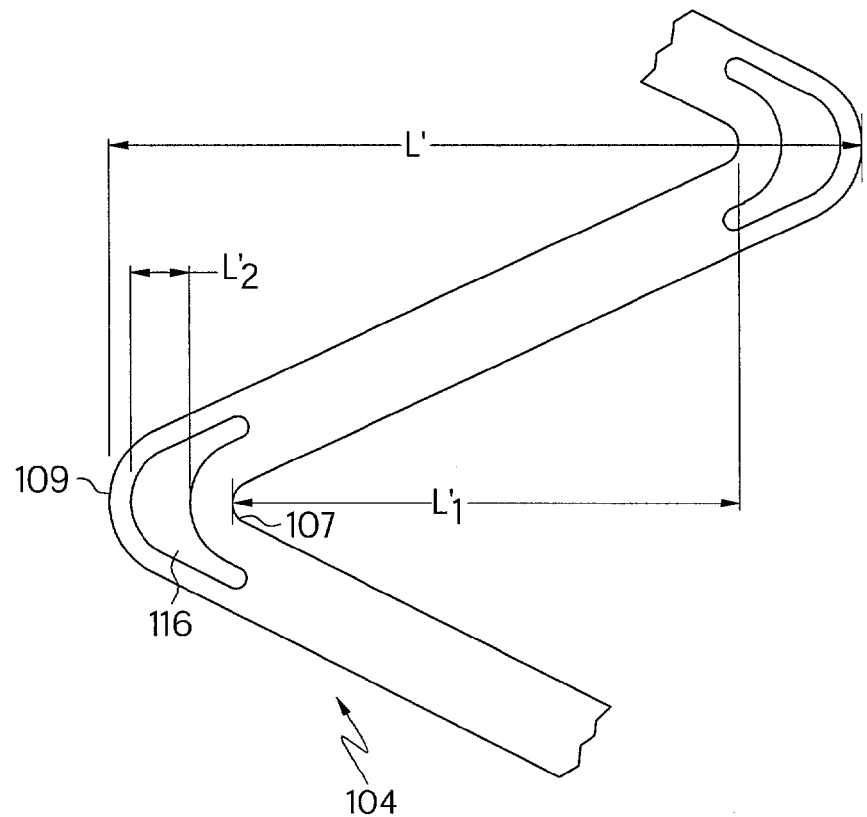
Figure 8B:
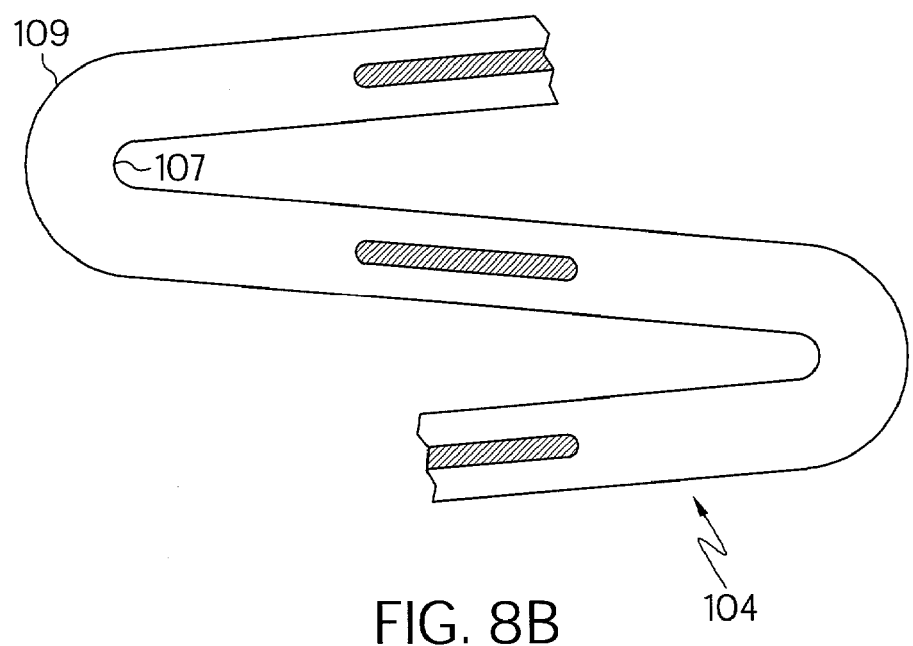
Figure 9B:
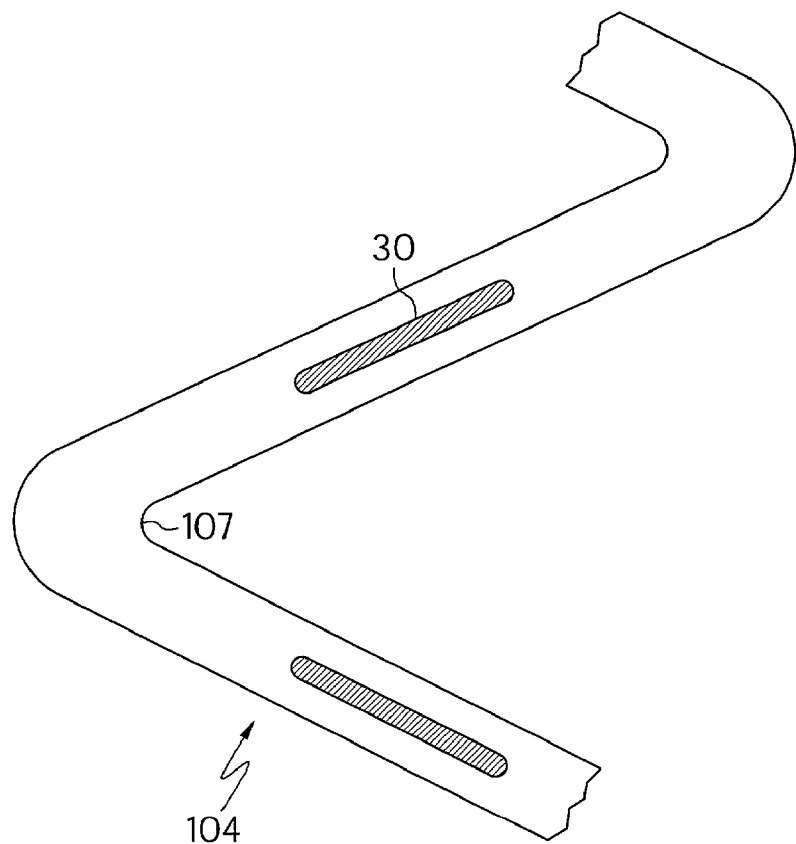
Figure 8C:
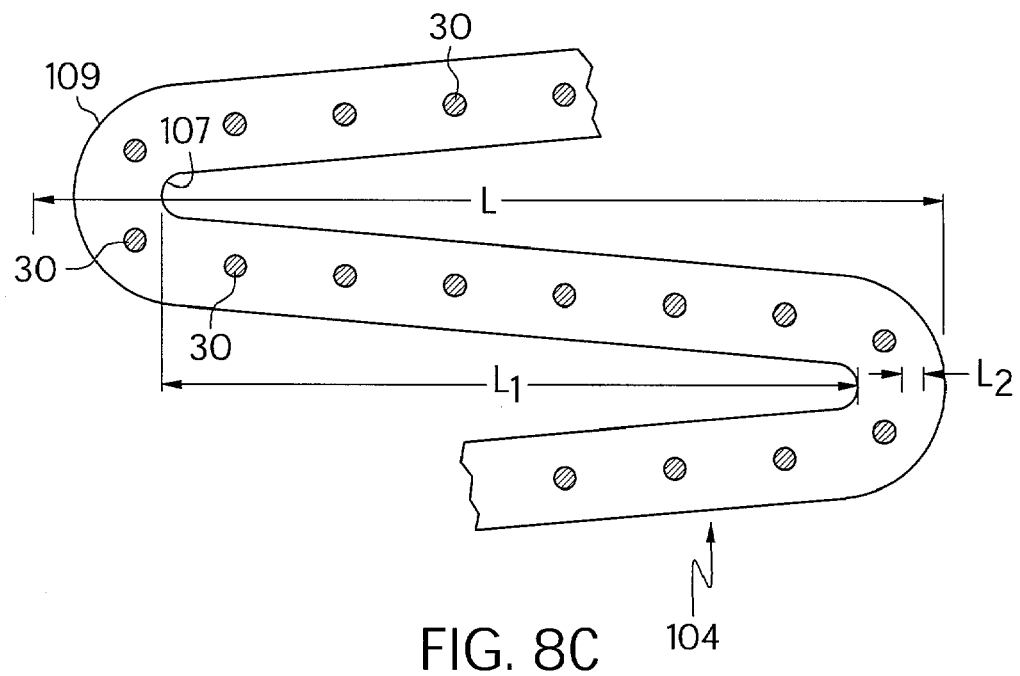
Figure 9C:
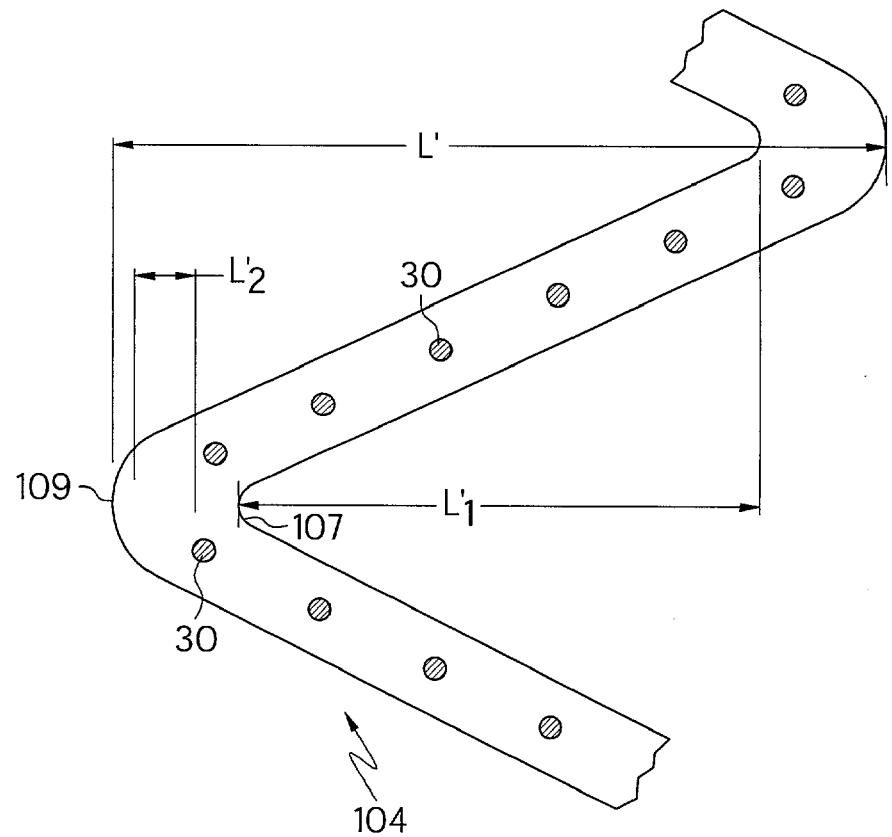

Upon expansion of the stent, as shown in FIG. 9a, the total longitudinal length of the expanded serpentine portion 104, denoted by L' is only slightly shorter than L. The decrease in longitudinal separation between the inner radii of the expanded serpentine portion, denoted by $L'_1$, is at least partially offset by the increase in the maximum separation between inner turn 107 and outer turn 109, denoted by $L'_2$.

It may further be desirable to employ the stents of the present invention for delivering substances into the body of a patient, particularly those wherein it is desirable to deliver at a target location within the body. FIG. 5a illustrates generally at 100 a typical stent geometry, and 5c illustrate generally at 100, a stent having connectors 112 and serpentine portions 104 forming the framework of the stent. Serpentine portion 104w exhibits variable depth recesses 30 of a substantially circular shape which provide a reservoir for holding a substance such as a therapeutic agent. FIG. 5c represents the same stent as shown in FIG. 5a but the shaped recesses are represented by an elongated ellipsoid rather than a substantially circular shape. A sideview of examples of a variable depth recess are shown at 103 in FIGS. 5b and 5d. As described above, the quantity of the recesses employed on the stent, the size of the recess, and the depth, may all be varied in order to control the amount of a substance that is deposited into the body. The recesses assist in preventing the substance from being disturbed during crimping, and all allow delivery of the substance to a target location without removal of the substance because it is located at subsurface.

FIGS. 6b to 9b and 6c to 9c illustrate alternative embodiments of a stent but having a geometry similar to the stents of FIGS. 6a–9a. In these embodiments, the cut-out regions of FIGS. 6a–9a, however, have been replaced with shaped recesses instead for delivery of a substance such as a therapeutic agent to a target location in the body of a patient. It is desirable that the shaped recesses therefore do not extend all the way through the serpentine portion 104 of stent 100.

FIGS. 6c, 7c, 8c and 9c represent stents which have a plurality of shaped recesses on both the turns 104a and the struts 104b of the serpentine portion 104.

Figure 10A:
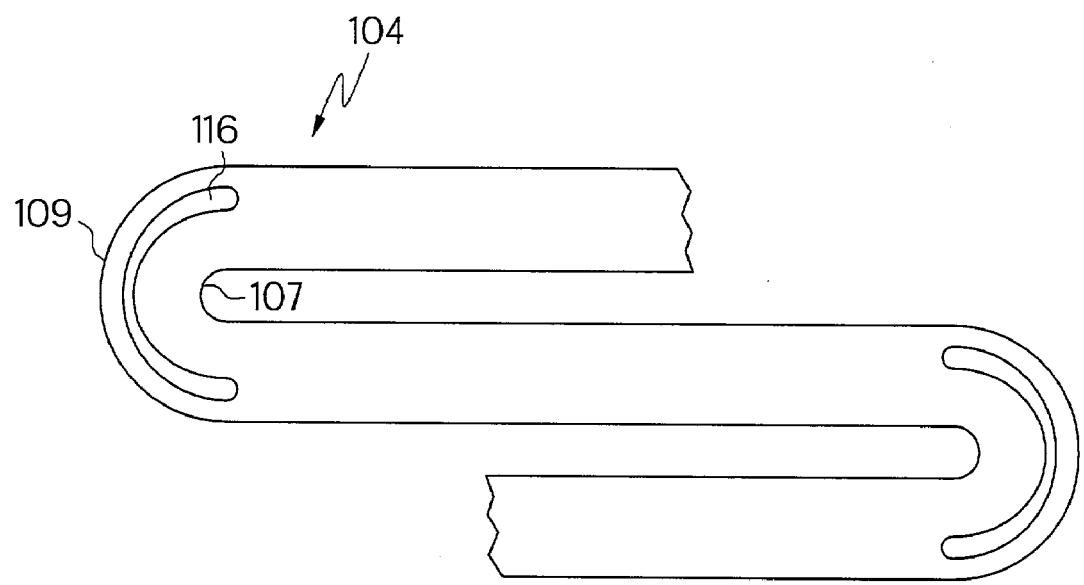
Figure 10B:
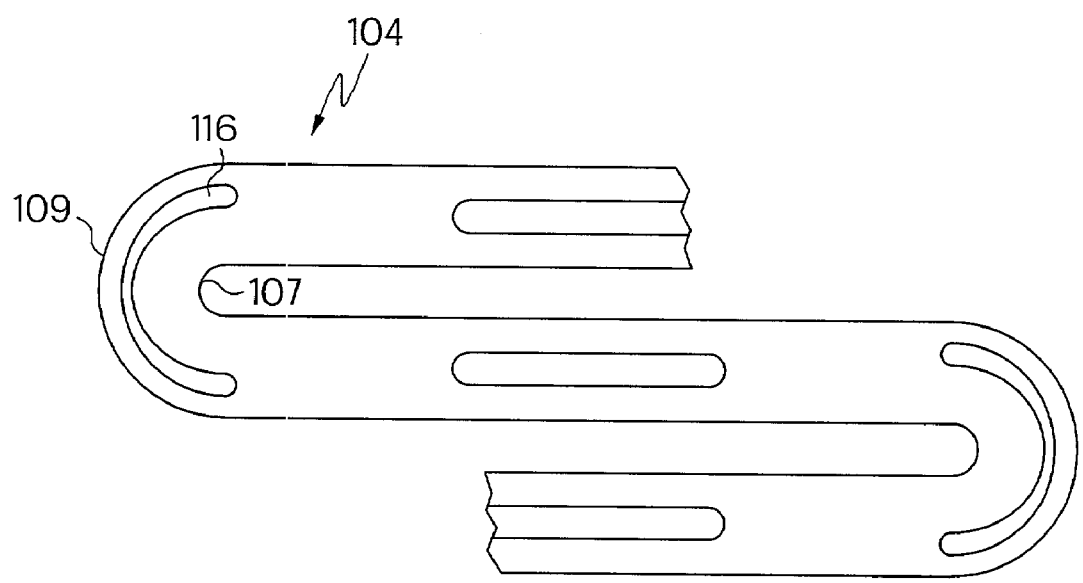
Figure 10C:
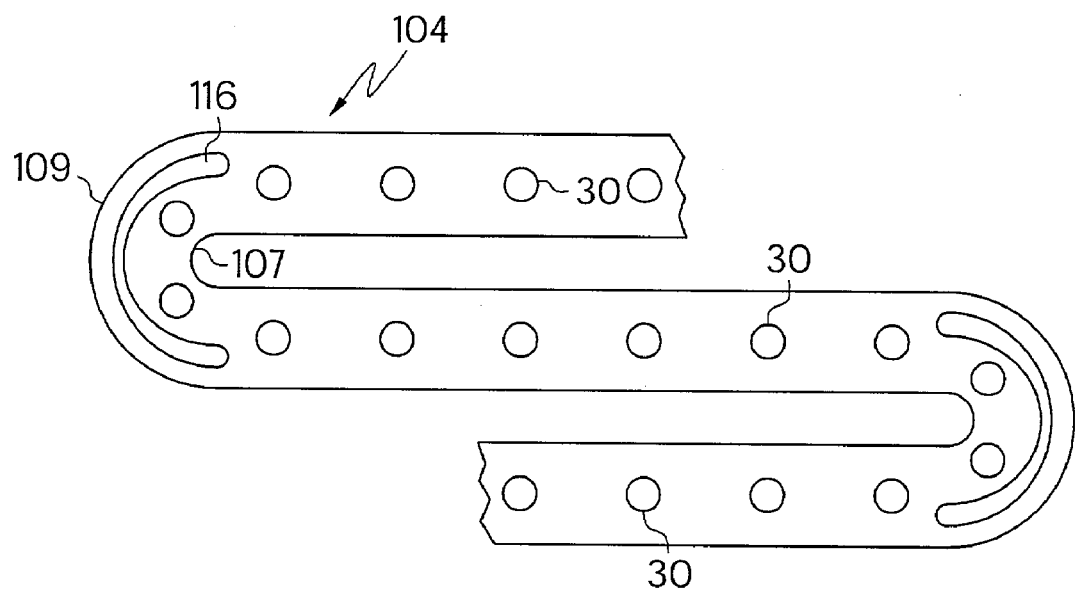
Figure 10D:
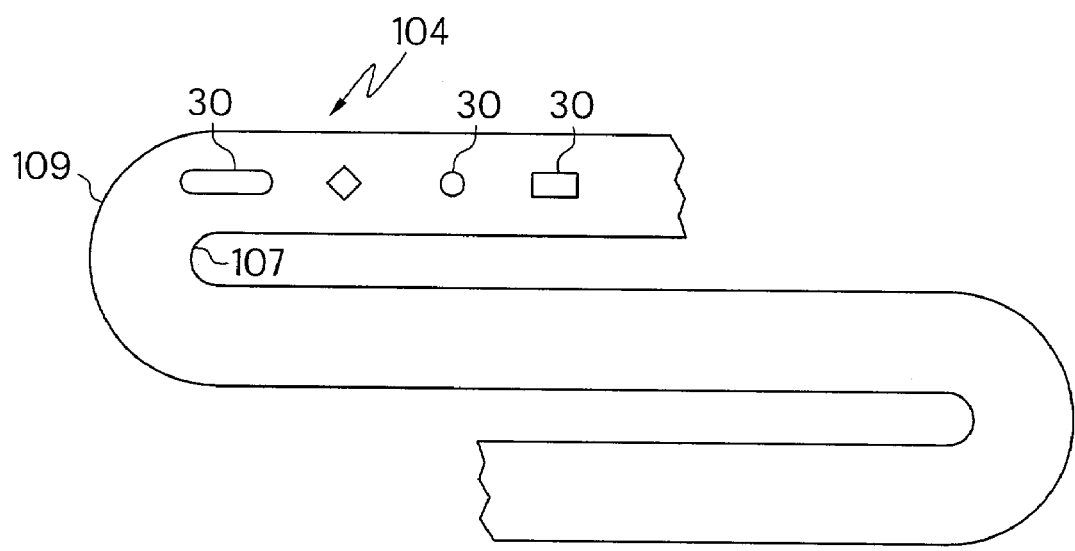
FIGS. 10d–10f illustrate the same stent configurations as in FIGS. 8a–10c, above, but with shaped recesses of varying patterns, sizes and geometries.
Figure 10E:
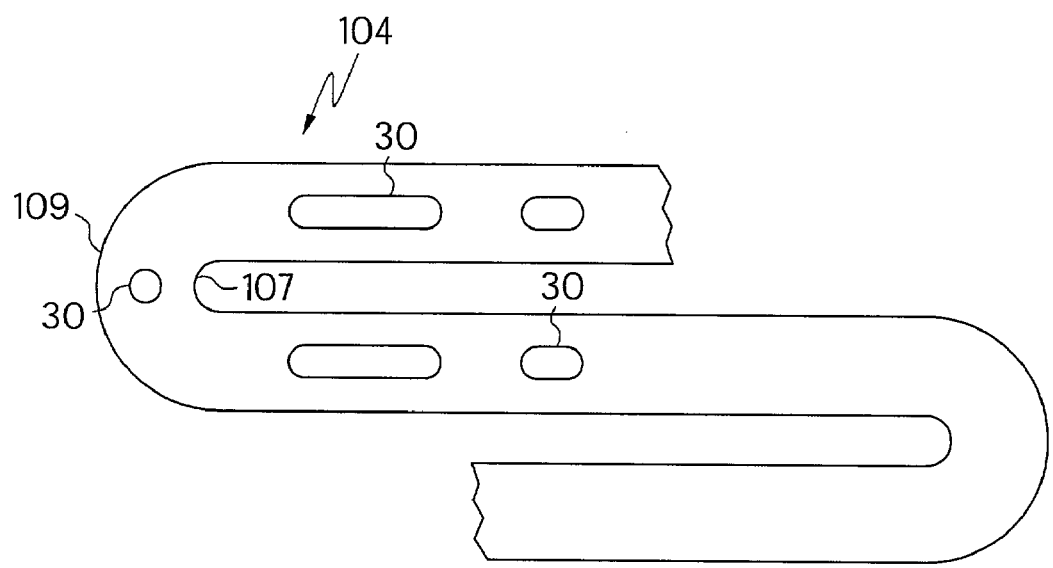
Figure 10F:
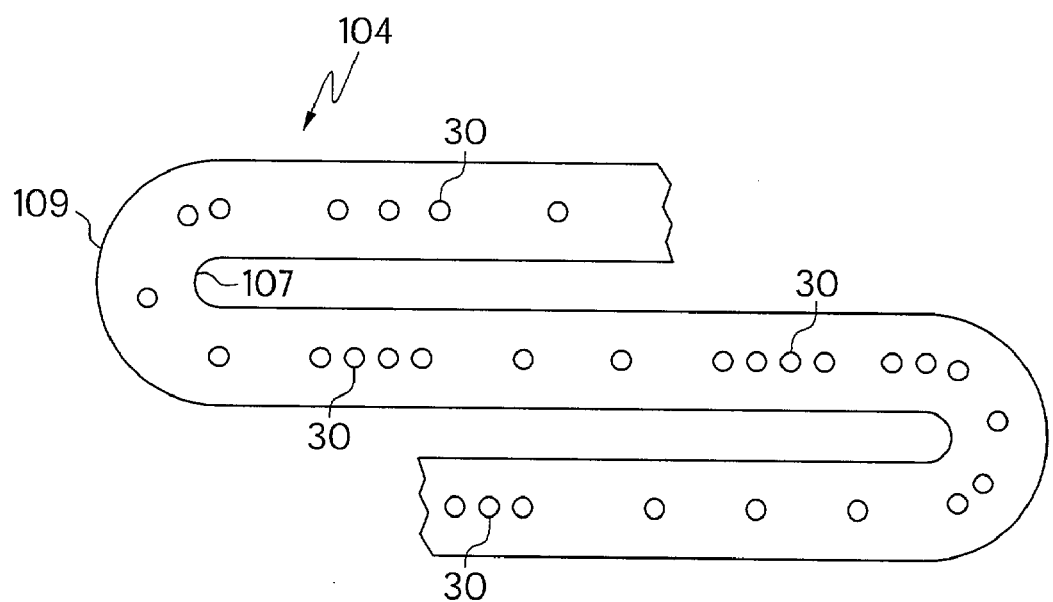

FIG. 10*f* is illustrate of an inventive stent of the present invention having a plurality of shaped recesses on both the turns 104*a* and the struts 104*b* of the serpentine portion 104. In this particular embodiment, the pattern of placement of the shaped recesses is irregular.

Further to the present invention, shaped recesses such as elongated ellipsoids and/or substantially circular recesses, or recesses of some other geometry may be provided on regions of the serpentine of the stent other than those shown in FIGS. 6*a*–9*a*. For example, in FIGS. 6*b*–9*b*, the elongated ellipsoids are found on the struts 104*b* of serpentine portion 104, while in FIGS. 6*c*–9*c*, the substantially circular recesses are found on both the curved sections 104*a* and the struts 104*b* of serpentine portion 104.

FIG. 10*a* shows the stent having cut-out areas in the turns. FIG. 10*b* illustrates elongated ellipsoid shaped recesses on the stent strut employed in combination with the cut-out regions in the turns. FIG. 10*c* illustrates the stent structure having cut-out regions in the turns and substantially circular shaped recesses on the stent struts. FIG. 10*d* illustrates shaped recesses of various geometries which may be employed. FIG. 10*e* illustrates that the pattern may include both elongated ellipsoids and substantially circular recesses on the same stent, as well as shaped recesses of different sizes. FIG. 10*f* illustrates that the shaped recesses may be placed along the stent strut in an irregular pattern.

In the case of a balloon expandable stent where cut-outs are employed as shown in FIGS. 10*a*–10*c*, during crimping of the stent, the size of cut-out region 116 decreases slightly and the spacing between inner turn 107 and outer turn 109 narrows. The decrease size of the cut-out region of the crimped stent compensates for the increase in length of the stent that may occur during crimping of the stent.

While the above figures are exemplary of the inventive, stents, it is important to note that other serpentine patterns may be employed as well. For example, the serpentine portions may have a constant cross-section along its length or may have a varying cross section along its length. In the latter case, the width and/or thickness of the serpentine portion may be varied along the length of the serpentine portion.

Figure 6B:
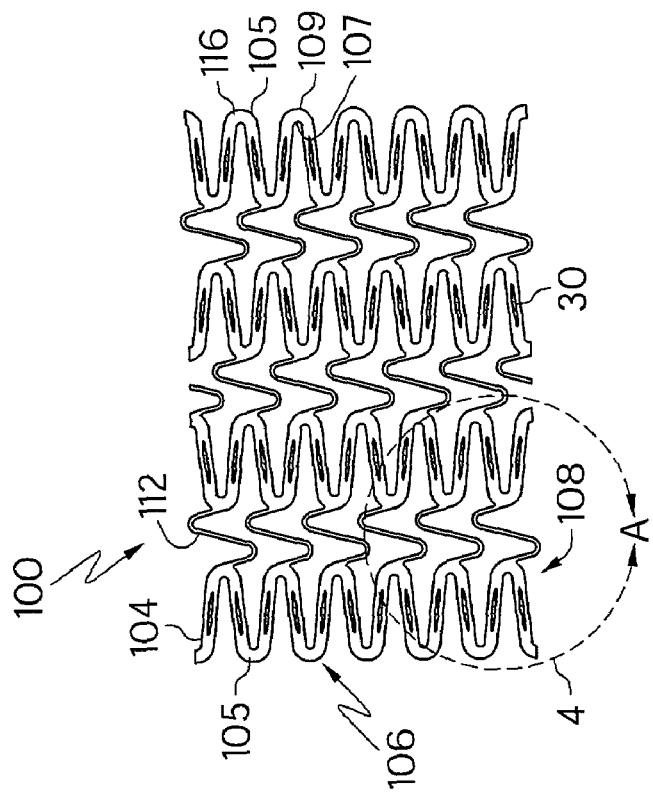
Figure 7B:
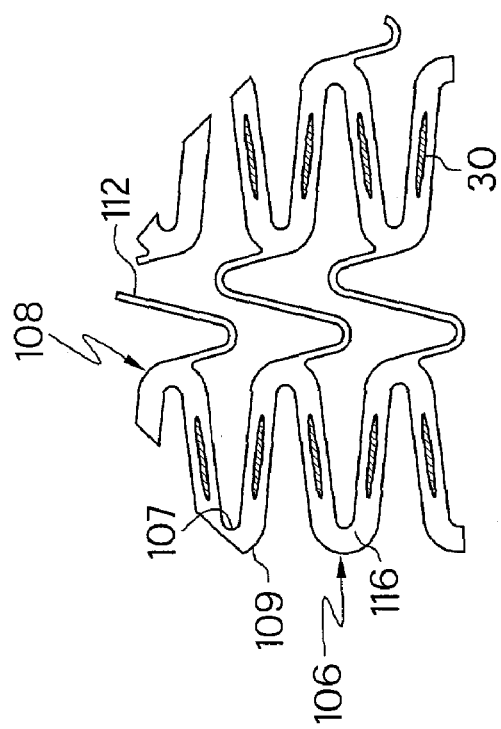
Figure 6C:
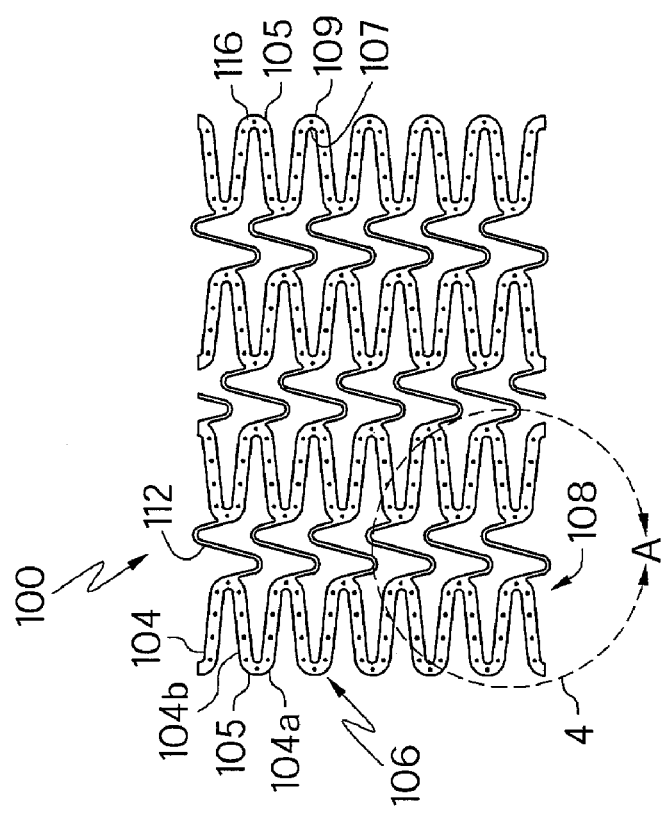
Figure 7C:
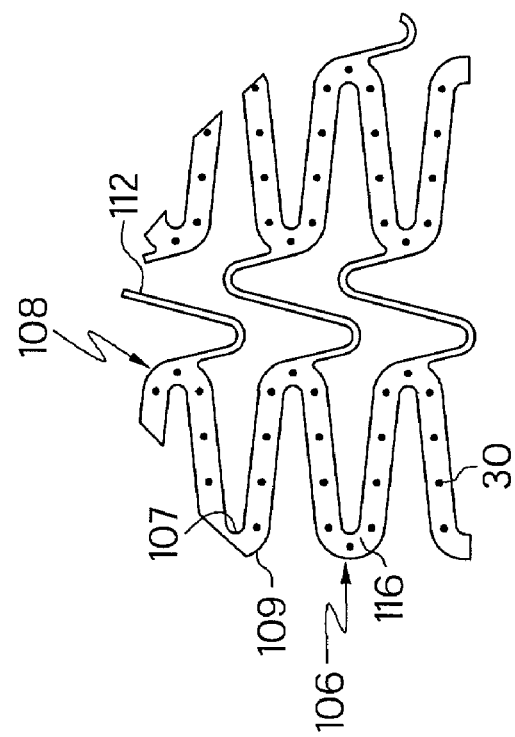

As shown in FIG. 6*a*–6*c*, for example, adjacent serpentine portions 104 are out of phase with one another. It is also within the scope of the invention for adjacent serpentine portions to be in phase with one another. More generally, adjacent serpentine portions may be provided in any phase relationship including 90 degrees and 180 degrees out of phase with one another.

Adjacent serpentine portions may be of the same frequency and/or amplitude or may be of different frequencies and/or amplitudes. An example of an inventive stent in which adjacent serpentine portions are of a different frequency and amplitude is shown generally at 100 in FIG. 11*a*. Serpentine portions 104*v*, 104*x* and 104*z* are of a first frequency and amplitude and serpentine portions 104*w* and 104*y* are of a second, higher frequency and smaller amplitude.

The stent of FIG. 11*b* includes cut-out regions 116 on serpentine 104*v*, 104*x* and 104*z* of the first frequency and amplitude and serpentine portions 104*w* and 104*y* of the second, higher frequency and smaller amplitude. Alternatively, the cut-out regions 116 may instead be elongated ellipsoids which do not extend all the way through the stent material.

Other shaped connectors may also be provided including substantially straight connectors, as shown in FIG. 11*a*, connectors which are curved and do not have any struts and connectors having one or more curved sections and one or more struts. Also, the first and second ends of each connector may be circumferentially aligned with one another, as shown in FIG. 11*c*, or circumferentially offset from one another as shown in FIG. 6*a*. An example of a linear connector whose first and seconds ends are circumferentially offset from one another and also is non-parallel to the longitudinal axis of the stent is shown in WO 9626689.

Each connector may have a constant cross-section along its length or may have a varying cross section along its length. In the latter case, the width and/or thickness of the connector may be varied along the length of the connector.

FIGS. 11*d*–11*i* illustrate the inventive stents of the type shown in FIGS. 11*a*–11*c* but the cut-out regions have been replaced with various shaped recesses which act as reservoirs for holding substances such as therapeutic agents. FIG. 11*d* illustrates an embodiment of the stent wherein elongated ellipsoid recesses are located along the struts 104*b* of the serpentine portions. The elongated ellipsoid recesses are shown on serpentine portions 104*v* and 104*z*. However, other shaped recesses may be located on any of the serpentines portions and in various combinations as will be illustrated by the following figures.

FIG. 11*e* shows an alternative embodiment in which the recesses are shown in a more circular shape and are located on both the curved sections 104*a* and the struts 104*b* of the serpentine portions. In this embodiment, the recesses are shown on serpentine 104*x*, but again may be located on any of the serpentine portions.

Shown in FIG. 11*f* is yet another alternative embodiment in which the shaped recesses include both elongated ellipsoids and substantially circular shaped recesses along the serpentine portions 104*v*–104*z*. The elongated ellipsoids and substantially circular shaped recesses are shown on both the curved sections 104*a* and the struts 104*b* of the serpentine portions.

FIG. 11*g* shows an alternative embodiment in which elongated ellipsoid shaped recesses are located along the struts 104*b* of serpentine portions 104*v*, 104*x* and 104*z*.

FIG. 11*h* illustrates an alternative embodiment in which the shaped recesses are triangular in shape and are located on the curved portions 104*a* of serpentine portions 104*w* and 104*y*.

FIG. 11*i* illustrates another alternative embodiment in which the shaped recesses are located along both the curved sections 104*a* and the struts 104*b* of serpentine portions 104*v*, 104*x* and 104*z*. The shaped recesses may be of various geometrical shapes and patterns, and the placement of the shaped recesses may vary as well. Further, size and depth may be varied as well.

The above figures are intended to be illustrative of only some of the shapes of the recessed areas and the patterns of placement on the stent and are not intended to limit the scope of the present invention. These features may be employed in endless shapes and patterns without departing from the scope of the present invention, and thus the above description should not be intended to limit the scope of the present invention.

The inventive stents may also be provided in embodiments in which there is a one-to-one relationship between the number of turns in a serpentine portion and the number of connectors, as shown in FIG. 6*a*, in embodiments in which there are fewer connectors than turns and in embodiments in which there are more connectors than turns.

Figure 12:
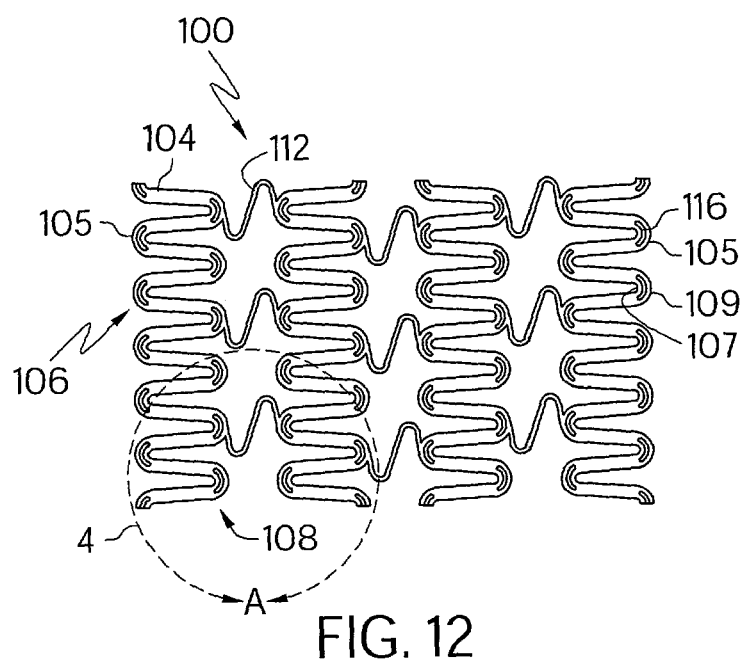

An example of the former is shown in FIG. 12. Every other pair of turns is connected in the stent of FIG. 12. The inventive stents may also be provided with other regular and irregular spacings of the connectors.

Stents having cut-out regions or shaped recesses of varying configurations or geometries in the regions of the turns are also within the scope of the invention, as are shaped recesses of various configurations and geometries located in the regions of the struts of the serpentine portions.

Figure 13:
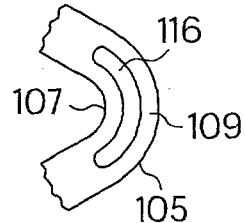
Figure 14:
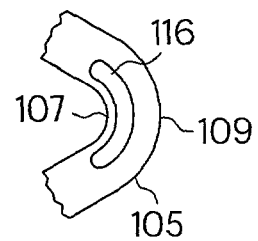
Figure 15:
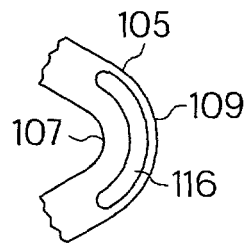

Another example of an inventive cut-out region in a turn of a serpentine portion of a stent is shown in FIG. 13. Cut-out region 116 in turn 105 is centered so that inner turn 107 is of the same width as outer turn 109. Cut-out region 116 may also be located closer to the inner diameter of turn 105 as shown in FIG. 14, resulting in inner turn 107 having a narrower width than outer turn 109. In another embodiment, cut-out region 116 is located closer to the outer diameter of turn 105 as shown in FIG. 15, resulting in inner turn 107 having a wider width than outer turn 109.

Figure 16:
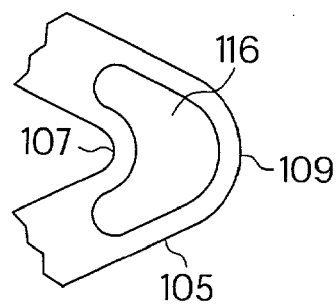

The size of cut-out region 116 may be altered to control the extent of foreshortening of the stent as well as to control the force needed to expand the stent in the case of a balloon expandable stent. An example of a wide cut-out region is shown in FIG. 16.

Figure 17A:
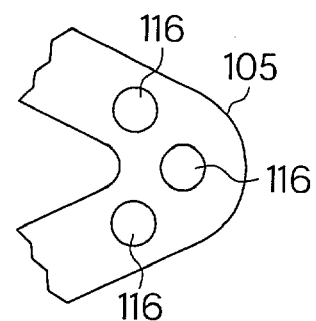
Figure 17B:
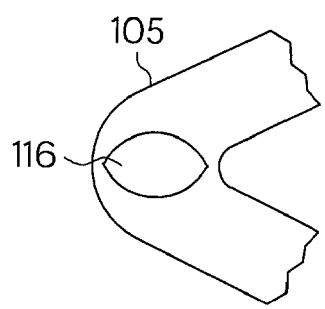
Figure 17C:
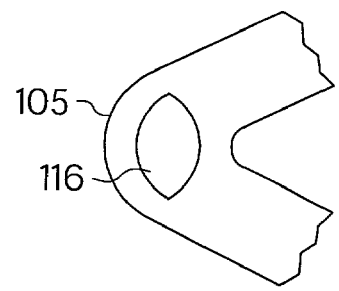
Figure 17D:
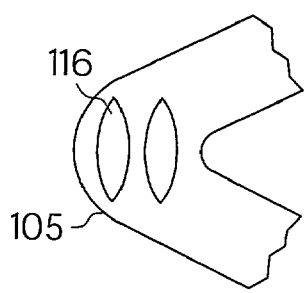
Figure 18:
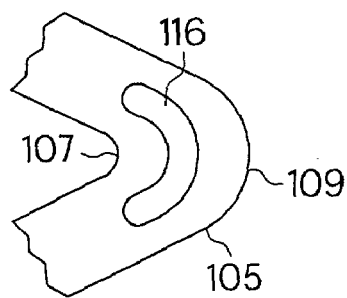

In accordance with the invention, more than one cut-out region may be provided in the vicinity of a turn. FIG. 17a shows an embodiment of the invention in which three circular cut-out regions 116 are provided in turn 105. Another embodiment of the invention in which multiple cut-outs are provided is shown in FIG. 17d. More generally, any of the stents disclosed herein may comprise multiple cut-outs in the vicinity of the turns.

In many of the embodiments of the invention disclosed herein, the cutout regions have a substantially arcuate appearance. Other shaped cut-outs may also be provided. By way of example only, an elliptical cut-out region having a major axis parallel to the longitudinal axis of the stent is shown at 116 in FIG. 17b. An elliptical cut-out region having a minor axis parallel to the longitudinal axis of the stent is shown at 116 in FIG. 17c. The presence of multiple elliptical cut-out regions in shown in FIG. 17d.

The length of the cut-out region may also be adjusted in accordance with the invention. For the cut-out regions in the turns of the serpentine portion, for example, a minimum length cut-out region 116 may be found, for example, in FIG. 17a while a maximum length cut-out region 116 may be found in FIG. 18, for example. Cut-out region 116 shown in FIG. 18 extends along the entire length of the radiuses portion of turn 105. It is noted that turn 105 includes a plurality of cut-out regions 116. Any of the other embodiments of the invention may be modified to provide a plurality of cut-out regions per turn. For example, in those embodiments of the invention in which the cut-out regions are arcuate, multiple arcuate regions may be provided.

Figure 19:
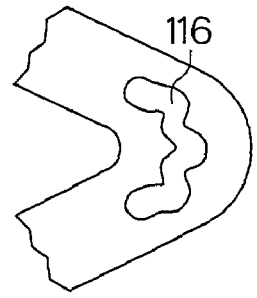
Figure 20:
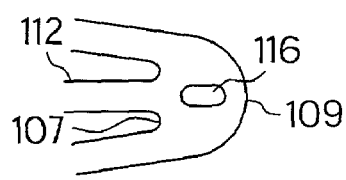
Figure 21:
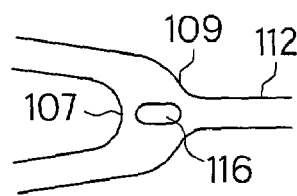

It is also within the scope of the invention for the cut-out region to have an irregular shape as shown in FIG. 19.

Where a connector extends from the turn, as shown in FIG. 20, cut-out region 116 may optionally be limited to the region of turn 105 corresponding to the longitudinal extension of connector 112. Connector 112 of FIG. 20 extends from the inner turn 107 or inner diameter of turn 105. An example of a larger cut-out region 116 which extends toward a connector 112 extending from inner turn 107 is shown in FIG. 21.

Figure 22:
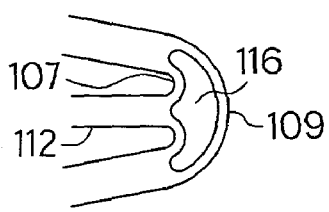
Figure 23:
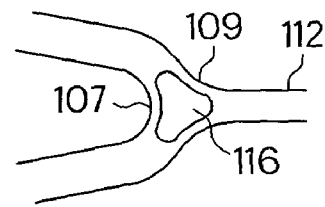

FIG. 22 illustrates a larger cut-out region 116 which extends into connector 112. Connector 112 extends from inner turn 107. FIG. 23 illustrates a larger cut-out region 116 which extends into connector 112 which, in turn, extends from outer turn 109.

As in previous embodiments, the cut-out regions as illustrated in FIGS. 13–23 may be replaced with recesses in the form of elongated ellipsoids or other shaped recesses that extend only partially through the stent at various depths rather than as cutouts which extend all the way through the stent. Furthermore, the stent may have some combination of cut-out regions and recesses.

Further to the present invention, cut-out regions or shaped recesses may be provided in all of the turns of the serpentine portions of the stent, as shown in FIG. 6a, or in only some of the turns of the serpentine portions. An example of a stent having serpentine portion with cut-out regions or shaped recesses in less than all of the turns is shown in FIG. 24.

In the stent of FIG. 24, the cut-out regions are disposed to facilitate opening of the proximal and distal ends of the stent first, while the elongated ellipsoid recesses are disposed to act as a reservoir for holding a substance such as a drug which is to be delivered to a target location in the body. The serpentine portions in the proximal end of the stent have cut-out regions or shaped recesses 30 in the proximal turns of the serpentines and the serpentine portions in the distal end of the stent have cut-out regions or shaped recesses 30 in the distal turns of the serpentines. Another embodiment of the invention in which the serpentine portions in the proximal end of the stent have cut-out regions 116 or shaped recesses 30 in the distal turns of the serpentines and the serpentine portions in the distal end of the stent have cut-out regions 116 or shaped recesses 30 in the proximal turns of the serpentines is shown in FIG. 25. If the stent as shown in FIG. 25 has cut-outs 116 rather than shaped recesses 30, it will open in the center prior to opening in the ends. More generally, individual serpentine portions of the stent may be provided with cut-out regions exclusively in the distal end of the serpentine or the proximal end of the serpentine to tailor the properties of the stent, depending on the opening properties desired, and whether or not the stent is also being employed for drug delivery.

It is also within the scope of the invention for adjacent cut-outs or shaped recesses to be spaced further apart along the serpentine portion. For example cut-out regions 116 or shaped recesses 30 may be provided at every third or fourth turn or may be spaced further apart.

It is further within the scope of the invention for adjacent pairs of cut-outs 116 or shaped recesses 30 to be spaced further apart along the serpentine portion. For example, as shown in FIG. 26, every other pair of turns 105 are provided with cut-out regions 116 or shaped recesses 30. Adjacent pairs of cut-out regions or shaped recesses may also be spaced further apart from one another along the serpentine portion 104 of stent 100. Other spacings of cut-out regions or shaped recesses are also within the scope of the invention.

It is also within the scope of the present invention, to replace any shaped recess with a shaped recess of a different shape. Varying the quantity, size, i.e. length and width, as well as the depth of the shaped recess may be employed to control the amount of a substance which will be deposited upon deployment of the stent.

More generally, it is within the scope of the invention to provide cut-out regions, elongated ellipsoids or other shaped recesses exclusively in some or all of the turns of the proximal and/or distal serpentine portions of the stent. The number of cut-out regions or shaped recesses in the inventive stents may be varied along the length of the stent, both in the on the struts and curved sections of the stent, and in turns of the serpentines may also be varied along the length of the stent.

In the case of a low opening pressure stent, the number of cut-out regions in the serpentine portions may decrease from the proximal and/or distal ends of the stent to the middle of the stent. Less pressure is required to expand those portions of the stent having more cut-out regions. This feature may provide desirable where a retaining sleeve is disposed about the proximal and/or distal ends of the stent.

To that end, the invention is also directed to stents having end serpentine portion(s) at the proximal and/or distal ends of the stent and intermediate serpentine portions between the end serpentine, where one or both of the end serpentine portions have more cut-out regions, elongated ellipsoids or other shaped recesses than the intermediate serpentine portions. Such as stent is shown by way of example in FIG. 11*a* or 11*d*. In the stent of FIG. 11*a*, the intermediate serpentine portions do not have any cut-out regions, elongated ellipsoids or other shaped recesses. Desirably, one or both of the end portions require less pressure to expand than the intermediate portions.

The invention is also directed to stents having end serpentine portion(s) at the proximal and/or distal ends of the stent and intermediate serpentine portions between the end serpentine, where one or both of the end serpentine portions have larger cut-out regions, elongated ellipsoids or other shaped recesses than the intermediate serpentine portions. Desirably, in the case of cut-out regions, one or both of the end portions require less pressure to expand than the intermediate portions.

The invention also is directed to embodiments in which the cut-out regions are designed and distributed such that the middle portion of the stent opens prior to one or both of the proximal and distal ends of the stent. For example, the middle portion of the stent may have more cut-out regions than one or both ends of the stent or may be provided with larger cut-out regions than one or both ends of the stent. An example of such a stent is shown in FIG. 11*b*. The stent of FIG. 11*b* has cut-outs only in the middle serpentine.

The cut-outs regions as described in the paragraph above, may be replaced with shaped recesses rather than cut-out regions for drug delivery, an example of which is shown in FIG. 11*e*. Of course, the substantially circular shaped recesses may be replaced with other geometric shapes including elongated ellipsoids, for example, as well.

The number of cut-out regions may also be adjusted to allow for increased stent securement in desired areas of the stent. Specifically, in the case of a balloon expandable stent, those regions of a stent lacking cut-out regions will typically have increased securement to a balloon catheter when crimped on a balloon and catheter than regions having cut-outs.

The cut-out regions that are provided in the turns of the inventive stents allow the turns of the stent to open more easily when a given force is applied thereto, thus facilitating expansion of the stent. This in turn, allows for wider struts to be employed, thereby increasing the radiopacity of the stent.

The invention is also directed to a radially expandable stent comprising a plurality of serpentine portions extending about the circumference of the stent, each serpentine portion having a plurality of turns where at least some of the turns and/or struts of the serpentine portions have at least some shaped recesses or wherein at least some of the turns have at least some fully enclosed cut-out regions and shaped recesses extending therethrough, or at least some of the turns have fully enclosed cut-out regions extending therethrough and some of the struts have at least some shaped recesses.

The shaped recesses are distributed about the stent so as to achieve optimum delivery of a drug upon deployment of the stent.

The cut-out regions may be distributed about the stent so that the stent opens in a non-uniform manner. Desirably, the stent includes a proximal serpentine portion at a proximal end of the stent, a distal serpentine portion at a distal end of the stent and a middle portion disposed between the proximal and distal ends of the stent and the cut-out regions are distributed such that the proximal and distal ends of the stent open prior to the middle portion of the stent. The cut-out regions may also be distributed such that the middle portion of the stent opens prior to one or both ends of the stent. Also desirably, the cut-out regions are substantially arcuate prior to expansion of the stent.

The invention is further directed to a stent such as that shown in FIG. 24 and many of the other figures disclosed herein comprising at least one tubular serpentine member 104 having a first end and a second end. The serpentine member has a plurality of turns 105 at the first end and a plurality of turns at the second end. Each of the turns at the first and second ends have a fully enclosed cut-out region extending therethrough, or elongated ellipsoid or other shaped recess 30. Typically, the stent will comprise a plurality of tubular serpentine members with adjacent tubular serpentine members connected one to the other. Desirably, the shape of the fully enclosed cut-out regions, elongated ellipsoid or some such other shaped recess is characterized by a first area when the stent is in an unexpanded configuration and by a second area when the stent is in an expanded configuration, the second area larger than the first area. The inventive stents may also be provided in embodiments in which the fully enclosed cut-out regions, or shaped recessed are characterized by a first width when the stent is in an unexpanded configuration and by a second width when the stent is in an expanded configuration, the second width greater than the first width. Typically, the cut-out regions, or other shaped recesses of the inventive stent will be arcuate when the stent is in the unexpanded state although cut-out regions or shaped recessed of other shapes as described above are also disclosed herein.

The inventive stents disclosed herein may be made of any suitable stent material including metals and polymeric materials as are known in the art. Suitable metals include stainless steels, tantalum, titanium, nitinol, Elgiloy and MP35N. Portions or the entirety of the inventive stents may be radiopaque. For example, a gold coating may be provided to selected regions or the entirety of the inventive stents.

The inventive stents may be laser cut, chemically etched, electrodischarge machined or cut using any other suitable technique from a tube. The stent pattern may also be cut into a sheet using any of the above-mentioned techniques or any other suitable technique, the sheet rolled into tubular form and the ends welded or otherwise joined together. The inventive stent designs may also be used in coiled sheet stents where the sheet which forms the stent is formed into a roll which may unroll to a wider opening.

It is further within the scope of the invention for the inventive stents disclosed herein to be provided with biocompatible coatings such as lubricious coating or other types of coatings known to those of skill in the art.

The entirety of the stent may be coated with the therapeutic agent, the cut-out regions only may be provided with the therapeutic agent, or the shaped recesses may be provided with the therapeutic agent, or some combination thereof. In one embodiment, one or more of the shaped recesses and/or cut-out regions will be filled with a therapeutic agent. It is also within the scope of the invention for only shaped recesses to be filled with a therapeutic agent. Moreover, in some embodiments of the invention, it may be desirable to have shaped recesses and/or cut-out regions including a therapeutic agent in one portion of the stent and cut-out regions without a therapeutic agent in another portion of the stent. For example, the shaped recesses and/or cut-out regions at one or both ends of the stent may include a therapeutic agent, and the cut-out regions in the middle of the stent may lack a therapeutic agent. As another example, the shaped recesses and/or cut-out regions in the middle of the stent may include a therapeutic agent and the cut-out regions in the ends of the stent may lack the agent. The shaped recesses and/or cut-out regions may be selectively filled by masking other portions of the stent and spraying, dipping or otherwise disposing therapeutic agent only in the shaped recesses or cut-out regions. For example, the stent may be placed on a mandril and masked so that the therapeutic agent may be disposed only in desired shaped recesses and/or cut-out regions of the stent.

In some embodiments of the present invention, it is desirable to provide only shaped recesses on the stent which are to be selectively filled with a therapeutic agent. The stent may optionally include cut-out regions to facilitate opening of the stent, but which do not have any therapeutic agent therein.

The inventive stents disclosed herein may be used in any suitable bodily vessel including the coronary arteries, the peripheral arteries, arteries of the neck, cerebral arteries, veins, biliary ducts, urethras, ureters, fallopian tubes, bronchial tubes, the trachea, the esophagus and the prostate. Its uses include supporting vessels in the region of lesions and vessels in the region of aneurisms. It is also particularly suited for use as an intracranial stent.

The invention is also directed to the combination of a inventive stent disclosed herein and a delivery catheter where a retaining sleeve is disposed about the proximal and/or distal end of the stent, as shown by way of example in FIG. 27. Catheter 200 includes stent 100 disposed about balloon 208 and catheter member 202. Retaining sleeves 204 are provided at the proximal and/or distal ends of the stent.

In one embodiment, stent 100 desirably has few and/or larger cut-out regions at the proximal and/or distal end to accommodate the additional force that is required to expand the stent in the region of the retaining sleeve.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below (e.g. claim 3 may be taken as alternatively dependent from claim 1 or claim 2; claim 4 may be taken as alternatively dependent from claim 1 or any of claims 2–3; claim 5 may be taken as alternatively dependent from claim 1 or any of claims 2–4; etc.).

This completes the description of the preferred and alternate embodiments of the invention. Those skilled in the art may recognize other equivalents to the specific embodiment described herein which equivalents are intended to be encompassed by the claims attached hereto.

The invention claimed is:

1. A stent comprising a first strut having a first side and a second side, each side having alternating crests and troughs wherein the crests of said first side of said first strut align with the troughs of said second side of said first strut, said first strut having a second strut adjacent said first strut, having a first side and a second side, each side having alternating crests and troughs wherein the crests of said first side of said second strut align with said troughs of said second side of said second strut, and said crests of said first side of said first strut align with said crests of said second side of said second strut and said troughs of said first side of said first strut align with said troughs of said second side of said second strut, the stent further comprising at least one turn having at least one shaped recess.

2. The stent of claim 1 wherein said first strut has a wave-like pattern.

3. The stent of claim 1 wherein said second strut has a wave-like pattern.

4. The stent of claim 1 having at least one shaped recess located between at least one crest and trough of said first strut.

5. The stent of claim 1 having at least one shaped recess located between a crest and a trough of said first strut and at least one shaped recess located between a crest and a trough of said second strut.

6. The stent of claim 1 wherein said at least one shaped recess is an elongated ellipsoid.

7. The stent of claim 1 wherein said at least one shaped recess has a substantially circular shape.

8. The stent of claim 1 wherein said at least one shaped recess contains a therapeutic agent.

9. The stent of claim 8 wherein said therapeutic agent is selected from the group consisting of genetic material, growth factors, antineoplastics, antimitotics, anti-inflammatories, antiplatelets, anticoagulants, antifibrins, antithrombins, antiproliferatives, antibiotics, antioxidants, and anti-allergenic substances.

10. The stent of claim 5 wherein the recess located between the crest and trough of said first strut and the recess located between the crest and trough of said second strut both contain a therapeutic agent.

11. The stent of claim 1 wherein a plurality of said struts have a plurality of shaped recesses thereon, and a plurality of turns have a plurality of shaped recesses thereon.

12. The stent of claim 1 having a plurality of shaped recesses having substantially circular and ellipsoid shapes.

13. The stent of claim 1 wherein at least one strut has more than one shaped recess thereon.

* * * * *